(12) United States Patent
Sullivan et al.

(10) Patent No.: US 12,179,032 B2
(45) Date of Patent: Dec. 31, 2024

(54) WEARABLE CARDIOVERTER DEFIBRILLATOR (WCD) SEGMENT BASED EPISODE OPENING AND CONFIRMATION PERIODS

(71) Applicant: West Affum Holdings Corp., Grand Cayman (KY)

(72) Inventors: Joseph L. Sullivan, Kirkland, WA (US); David P. Finch, Bothell, WA (US); Douglas K. Medema, Everett, WA (US); Robert R. Buchanan, Bothell, WA (US); Garrett M. Kotlarchik, Kenmore, WA (US); Jaeho Kim, Redmond, WA (US); Kenneth F. Cowan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 324 days.

(21) Appl. No.: 17/546,892

(22) Filed: Dec. 9, 2021

(65) Prior Publication Data
US 2022/0143389 A1    May 12, 2022

Related U.S. Application Data

(60) Continuation-in-part of application No. 17/503,065, filed on Oct. 15, 2021, now Pat. No. 11,844,953, (Continued)

(51) Int. Cl.
*A61N 1/39*    (2006.01)
*A61B 5/00*    (2006.01)
(Continued)

(52) U.S. Cl.
CPC ........ *A61N 1/39046* (2017.08); *A61B 5/0245* (2013.01); *A61B 5/282* (2021.01);
(Continued)

(58) Field of Classification Search
CPC ............................................. A61N 1/39–3993
See application file for complete search history.

(56) References Cited

U.S. PATENT DOCUMENTS 3,724,455 A    4/1973    Unger
4,291,699 A    9/1981    Geddes et al.
(Continued)

FOREIGN PATENT DOCUMENTS

| CA | 2942933 A1 | 8/2015 |
| CN | 103405851 A | 11/2013 |
| WO | 9839061 A2 | 9/1998 |

OTHER PUBLICATIONS

U.S. Appl. No. 15/880,853, filed Jan. 26, 2018, Joseph L. Sullivan.
(Continued)

*Primary Examiner* — Eric D. Bertram
(74) *Attorney, Agent, or Firm* — Spectrum IP Law Group LLC

(57) ABSTRACT

A wearable cardioverter defibrillator (WCD) comprises a plurality of electrocardiography (ECG) electrodes. An episode is opened responsive to a string of consecutive segments meeting one or more shock criteria, and a shockable rhythm is confirmed for the episode responsive to a subsequent string of consecutive segments meeting one or more confirmation criteria.

21 Claims, 21 Drawing Sheets

Related U.S. Application Data which is a division of application No. 16/382,575, filed on Apr. 12, 2019, now Pat. No. 11,160,990.

(60) Provisional application No. 62/630,695, filed on Feb. 14, 2018.

(51) Int. Cl.
| | |
|---|---|
| *A61B 5/0245* | (2006.01) |
| *A61B 5/282* | (2021.01) |
| *A61B 5/316* | (2021.01) |
| *A61B 5/341* | (2021.01) |
| *A61B 5/361* | (2021.01) |
| *A61B 5/363* | (2021.01) |
| *A61B 5/366* | (2021.01) |
| *A61N 1/02* | (2006.01) |
| *A61N 1/04* | (2006.01) |

(52) U.S. Cl.
CPC .............. *A61B 5/316* (2021.01); *A61B 5/341* (2021.01); *A61B 5/361* (2021.01); *A61B 5/363* (2021.01); *A61B 5/366* (2021.01); *A61B 5/4836* (2013.01); *A61B 5/7203* (2013.01); *A61N 1/025* (2013.01); *A61N 1/046* (2013.01); *A61N 1/0484* (2013.01); *A61N 1/3987* (2013.01); *A61N 1/3993* (2013.01); *A61B 2562/0214* (2013.01); *A61B 2562/0215* (2017.08)

(56) References Cited

U.S. PATENT DOCUMENTS

| | | |
|---|---|---|
| 4,583,524 A | 4/1986 | Hutchins |
| 4,617,938 A | 10/1986 | Shimoni et al. |
| 4,619,265 A | 10/1986 | Morgan et al. |
| 4,895,151 A | 1/1990 | Grevis et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,376,104 A | 12/1994 | Sakai et al. |
| 5,381,803 A | 1/1995 | Herleikson et al. |
| 5,394,892 A | 3/1995 | Kenny et al. |
| 5,405,362 A | 4/1995 | Kramer et al. |
| 5,425,749 A | 6/1995 | Adams |
| 5,474,574 A | 12/1995 | Payne et al. |
| 5,554,174 A | 9/1996 | Causey, III |
| 5,601,612 A | 2/1997 | Gliner et al. |
| 5,630,834 A | 5/1997 | Bardy |
| 5,662,690 A | 9/1997 | Cole et al. |
| 5,709,215 A | 1/1998 | Perttu et al. |
| 5,769,872 A | 6/1998 | Lopin et al. |
| 5,782,878 A | 7/1998 | Morgan et al. |
| 5,792,204 A | 8/1998 | Snell |
| 5,803,927 A | 9/1998 | Cameron et al. |
| 5,819,007 A | 10/1998 | Elghazzawi |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,068,651 A | 5/2000 | Brandell |
| 6,108,197 A | 8/2000 | Janik |
| 6,148,233 A * | 11/2000 | Owen .................. A61N 1/0476 607/5 |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,351,671 B1 | 2/2002 | Myklebust et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,694,187 B1 | 2/2004 | Freeman |
| 6,762,917 B1 | 7/2004 | Verbiest et al. |
| 6,941,168 B2 | 9/2005 | Girouard |
| 7,065,401 B2 | 6/2006 | Worden |
| 7,149,576 B1 | 12/2006 | Baura et al. |
| 7,336,994 B2 | 2/2008 | Hettrick et al. |
| 7,379,771 B2 | 5/2008 | Kovac et al. |
| 7,460,900 B1 | 12/2008 | Gill et al. |
| 7,559,902 B2 | 7/2009 | Ting et al. |
| 7,865,238 B2 | 1/2011 | Brink |
| 7,870,761 B2 | 1/2011 | Valentine et al. |
| 7,894,894 B2 | 2/2011 | Stadler et al. |
| 7,974,689 B2 | 7/2011 | Volpe et al. |
| 8,024,037 B2 | 9/2011 | Kumar |
| 8,036,746 B2 | 10/2011 | Sanders |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,825,154 B2 | 9/2014 | Jorgenson et al. |
| 8,838,235 B2 | 9/2014 | Cowan et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 8,996,101 B2 | 3/2015 | Zhang et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,533,165 B1 | 1/2017 | Gunderson |
| 9,592,403 B2 | 3/2017 | Sullivan |
| 9,757,579 B2 | 9/2017 | Foshee, Jr. et al. |
| 9,757,581 B2 | 9/2017 | Sullivan et al. |
| 10,016,614 B2 | 7/2018 | Sullivan |
| 10,322,291 B2 | 6/2019 | Medema et al. |
| 11,077,310 B1 | 8/2021 | Sullivan |
| 11,103,717 B2 | 8/2021 | Sullivan et al. |
| 11,160,990 B1 | 11/2021 | Sullivan et al. |
| 11,331,508 B1 | 5/2022 | Cowan et al. |
| 2011/0022105 A9 | 1/2003 | Owen et al. |
| 2003/0158593 A1 | 8/2003 | Heilman et al. |
| 2003/0187479 A1 | 10/2003 | Thong |
| 2004/0049117 A1 | 3/2004 | Ideker et al. |
| 2004/0220623 A1 | 11/2004 | Hess |
| 2004/0230105 A1 | 11/2004 | Geva et al. |
| 2005/0107833 A1 | 5/2005 | Freeman et al. |
| 2005/0107834 A1 | 5/2005 | Freeman et al. |
| 2005/0131476 A1 | 6/2005 | Kim et al. |
| 2006/0017575 A1 | 1/2006 | McAdams |
| 2006/0173364 A1 | 8/2006 | Clancy et al. |
| 2007/0179539 A1 | 8/2007 | DeGroot et al. |
| 2007/0203418 A1 | 8/2007 | Starc |
| 2008/0033495 A1 | 2/2008 | Kumar |
| 2008/0208070 A1 | 8/2008 | Snyder et al. |
| 2008/0215103 A1 | 9/2008 | Powers et al. |
| 2008/0306560 A1 | 12/2008 | Macho et al. |
| 2008/0312708 A1 | 12/2008 | Snyder |
| 2008/0312709 A1 | 12/2008 | Volpe et al. |
| 2009/0005827 A1 | 1/2009 | Weintraub et al. |
| 2009/0018595 A1 | 1/2009 | Bharmi et al. |
| 2010/0007413 A1 | 1/2010 | Herleikson et al. |
| 2010/0114248 A1 | 5/2010 | Donofrio et al. |
| 2010/0298899 A1 | 11/2010 | Donnelly et al. |
| 2010/0331904 A1 | 12/2010 | Warren et al. |
| 2011/0202101 A1 * | 8/2011 | Tan ..................... G09B 19/003 607/7 |

(56) References Cited

U.S. PATENT DOCUMENTS

| | | |
|---|---|---|
| 2011/0288604 A1 | 11/2011 | Kaib et al. |
| 2011/0288605 A1 | 11/2011 | Kaib et al. |
| 2012/0022355 A1 | 1/2012 | Byrd et al. |
| 2012/0150008 A1 | 1/2012 | Lanar et al. |
| 2012/0059270 A1 | 3/2012 | Grunwald |
| 2012/0108911 A1 | 5/2012 | Drysdale et al. |
| 2012/0112903 A1 | 5/2012 | Kaib et al. |
| 2012/0144551 A1 | 6/2012 | Guldalian |
| 2012/0158075 A1 | 6/2012 | Kaib et al. |
| 2012/0265265 A1 | 10/2012 | Razavi et al. |
| 2012/0277638 A1 | 11/2012 | Skelton et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2012/0316611 A1 | 12/2012 | Armoundas et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0025132 A1 | 1/2014 | Libbus et al. |
| 2014/0070957 A1 | 3/2014 | Longinotti-Buitoni et al. |
| 2014/0081162 A1 | 3/2014 | Snell et al. |
| 2014/0150781 A1 | 6/2014 | Capua et al. |
| 2014/0163395 A1 | 6/2014 | Sapp, Jr. et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0037636 A1 | 2/2015 | Amsler et al. |
| 2015/0039053 A1 | 2/2015 | Kaib et al. |
| 2015/0105835 A1 | 4/2015 | Thakur et al. |
| 2015/0265845 A1 | 9/2015 | Sullivan et al. |
| 2015/0273227 A1* | 10/2015 | Zhang .................. A61N 1/3925 607/7 |
| 2015/0273229 A1* | 10/2015 | Zhang .................. A61B 5/363 607/7 |
| 2015/0297107 A1 | 10/2015 | Sullivan et al. |
| 2015/0328472 A1 | 11/2015 | Sullivan et al. |
| 2016/0000349 A1 | 1/2016 | Sullivan et al. |
| 2016/0004831 A1 | 1/2016 | Carlson et al. |
| 2016/0007877 A1 | 1/2016 | Felix et al. |
| 2016/0015329 A1 | 1/2016 | Kohlrausch et al. |
| 2016/0067514 A1 | 3/2016 | Sullivan |
| 2016/0074667 A1 | 3/2016 | Sullivan et al. |
| 2016/0082277 A1* | 3/2016 | Foshee, Jr. ........... A61N 1/0484 607/5 |
| 2016/0106332 A1 | 4/2016 | Takeshima |
| 2016/0121100 A1 | 5/2016 | Crone et al. |
| 2016/0220833 A1* | 8/2016 | Tan ........................ A61B 5/11 |
| 2016/0235320 A1 | 8/2016 | Sarkar et al. |
| 2016/0278698 A1 | 9/2016 | Freeman et al. |
| 2016/0331984 A1 | 11/2016 | Firoozabadi et al. |
| 2016/0353996 A1 | 12/2016 | Fink |
| 2017/0056682 A1 | 3/2017 | Kumar et al. |
| 2017/0157416 A1 | 6/2017 | Medema et al. |
| 2017/0225001 A1* | 8/2017 | Zaidi ..................... A61B 5/053 |
| 2017/0252571 A1 | 9/2017 | Dascoli et al. |
| 2018/0028083 A1 | 2/2018 | Greenhut et al. |
| 2018/0093102 A1 | 4/2018 | Sullivan et al. |
| 2018/0116537 A1 | 5/2018 | Sullivan et al. |
| 2018/0117299 A1 | 5/2018 | Gustavson et al. |
| 2018/0153765 A1* | 6/2018 | Freeman .................. A61B 5/02 |
| 2018/0184933 A1* | 7/2018 | Sullivan ................. A61B 5/316 |
| 2018/0185662 A1* | 7/2018 | Foshee, Jr. ........... A61B 5/4809 |
| 2018/0221648 A1 | 8/2018 | Gustavson et al. |
| 2018/0264279 A1 | 9/2018 | Kim et al. |
| 2018/0318593 A1 | 11/2018 | Sullivan |
| 2019/0030351 A1 | 1/2019 | Sullivan et al. |
| 2019/0030352 A1 | 1/2019 | Sullivan et al. |
| 2020/0164217 A1 | 5/2020 | Sullivan |
| 2022/0032077 A1 | 2/2022 | Sullivan et al. |

OTHER PUBLICATIONS

U.S. Appl. No. 16/268,870, filed Feb. 6, 2019, Joseph L. Sullivan.
U.S. Appl. No. 16/360,984, filed Mar. 21, 2019, Joseph L. Sullivan.
U.S. Appl. No. 16/366,313, filed Mar. 27, 2019, Joseph L. Sullivan.
U.S. Appl. No. 16/554,410, filed Aug. 28, 2019, Joseph L. Sullivan.
U.S. Appl. No. 62/630,398, filed Feb. 14, 2018, Sullivan.
Duncker et al. "Real-world Experience of 355 Consecutive Patients with a Wearable Cardioverter/Debrillator—Single Centre Analysis" Europace 2017, No. 19 Supplemental 3, iii304.
EPO Search Report mailed Dec. 19, 2018 on EP Application No. 1816221.0-1224.
EPO Search report mailed Sep. 27, 2018 on EP Application 18186229.3-1224.
European Search Report of European Application 16202067.1-1666, dated Apr. 25, 2017.
First Office action and Search Report issued on Aug. 30, 2018, to CN Patent Application No. 2016111063501.
Heartstart MRx and XL AED Algorithm—Application Note, Jul. 2001, Edition 2 Philips Healthcare, USA.
Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
Lifecor LifeVest System Model WCD 3100 Operator's Manual, 2006, PN 20B0040 Rev FI, Zoll Lifecor Corporation, Pittsburgh, PA.
LifeVest Model 4000 Patient Manual, Zoll, 2009, PN 20B0047 Rev B.
Olgin JE, Pletcher MJ, Vittinghoff E, et al., "Wearable Cardioverter-Defibrillator after Myocardial Infarction," N Engl J Med Sep. 27, 2018; 379(13):1205-1215.
Pagan-Carlo, et al., "Encircling Overlapping Multipulse Shock Waveforms for Transthoracic Defibrillation," JACC Journals, Dec. 1998, vol. 32 Issue 7, p. 2065-2071.
Schuhmann et al., "Experience with the wearable cardioverter defibrillator (WCD) in high risk cardiac patients from a German single center cohort", Heart Rhythm 2016;13(5):S254.
Second Office Action issued on May 18, 2020, to CN Patent Application No. 2016111106350.1.
The LifeVest Network/Patient Data Management System, Zoll, 2015, 2000503 Rev A.
WCD Performance for Clinical Review, Sullivan et al., "A Novel Wearable Cardioverter Defibrillator With Reduced False Alarm Rate," AHA 2017.

\* cited by examiner

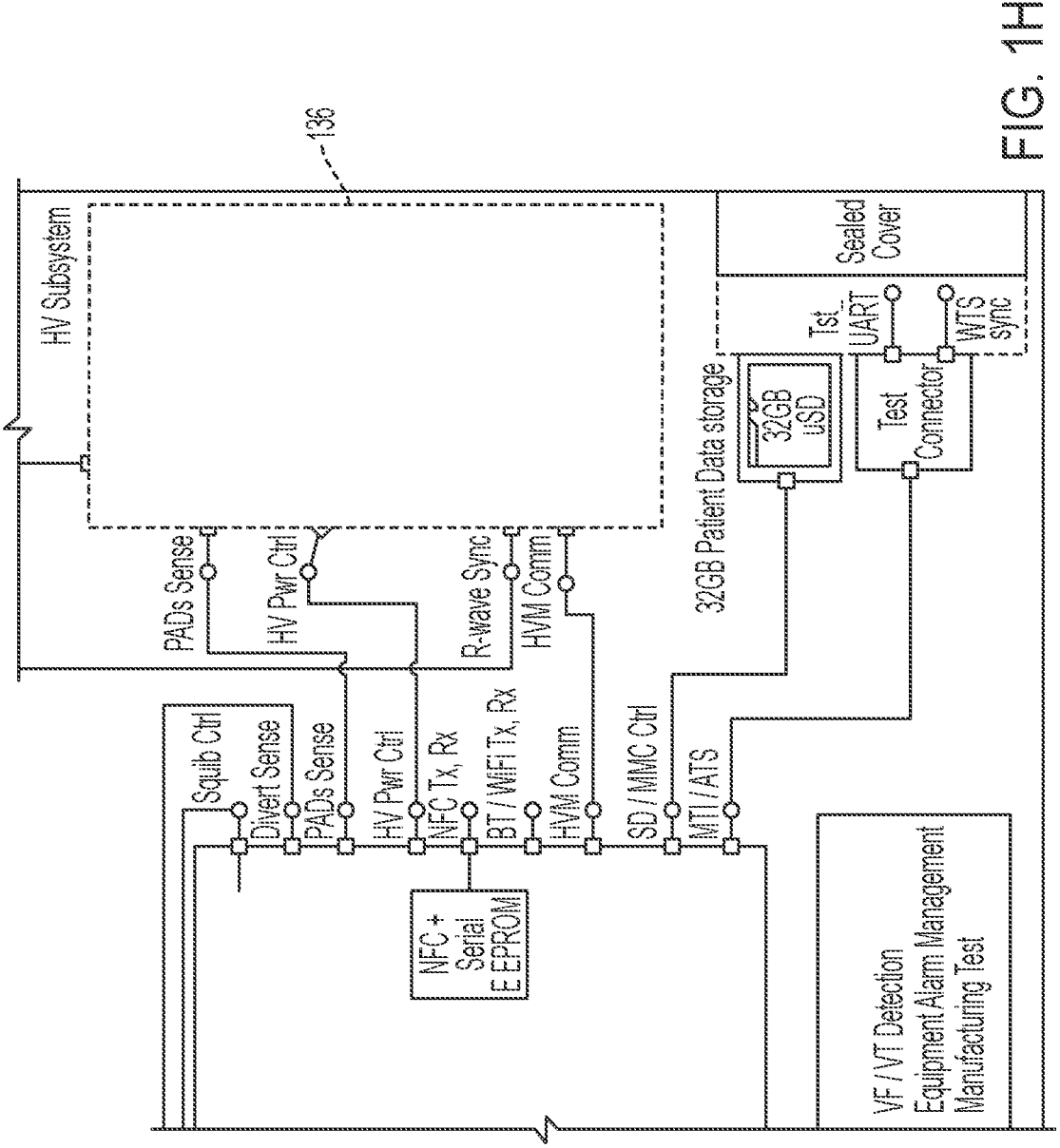

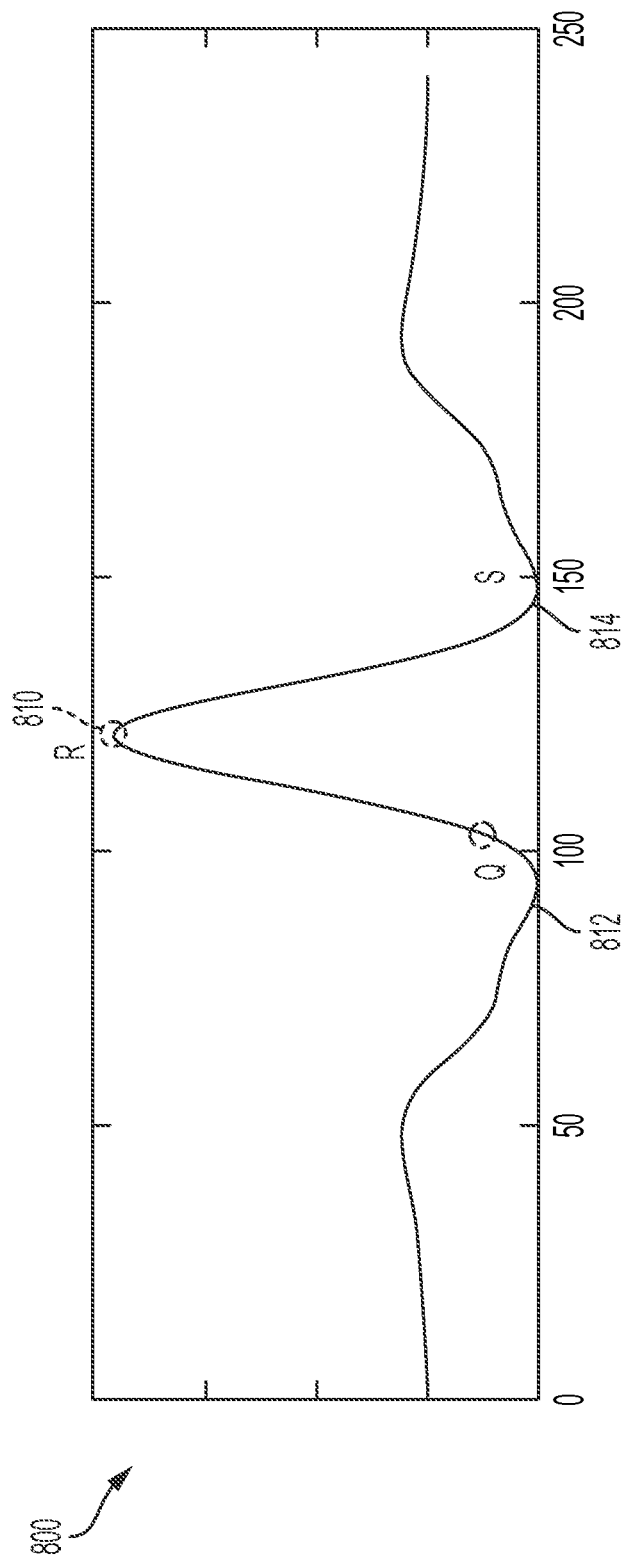

WEARABLE CARDIOVERTER DEFIBRILLATOR (WCD) SEGMENT BASED EPISODE OPENING AND CONFIRMATION PERIODS

CROSS-REFERENCE TO RELATED APPLICATIONS

The present application is continuation-in-part of U.S. application Ser. No. 17/503,065 filed Oct. 15, 2021 (pending), which is a divisional of U.S. application Ser. No. 16/382,575 filed Apr. 12, 2019 (now U.S. Pat. No. 11,160,990 issued Nov. 2, 2021), which in turn claims the benefit of U.S. Provisional Application No. 62/630,695 filed Feb. 14, 2018. Said U.S. Pat. No. 11,160,990, said application Ser. No. 16/382,575, said application Ser. No. 17/503,065, and said Application No. 62/630,695 are hereby incorporated herein by reference in their entireties for all purposes.

BACKGROUND

Conventional wearable cardioverter defibrillators (WCDs) analyze patient signals to determine if the patient is experiencing a cardiac arrest. If a ventricular tachycardia/ventricular fibrillation (VT/VF) arrest is suspected, the WCD will alarm to warn the patient and bystanders of an impending shock. Conventional WCDs often alarm inappropriately, for example when the patient is not in cardiac arrest. It has been found that the only commercially available WCD with published clinical performance gives an inappropriate or false shock alarm about once every three patient-days on average. These inappropriate or false alarms can be distressing for the patient and could lead to an unnecessary shock if the patient does not take action to intervene before the shock is applied. If the false alarm rate is too high, then the patient is likely to discontinue wearing the WCD.

DESCRIPTION OF THE DRAWING FIGURES

Claimed subject matter is particularly pointed out and distinctly claimed in the concluding portion of the specification. However, such subject matter may be understood by reference to the following detailed description when read with the accompanying drawings in which:

FIG. 1A through FIG. 1H illustrate a diagram of a wearable cardioverter defibrillator (WCD) in accordance with one or more embodiments.

FIG. 8 is a diagram of an example QRS complex as part of a QRS width measuring process used in a WCD in accordance with one or more embodiments.

Figure 1A:
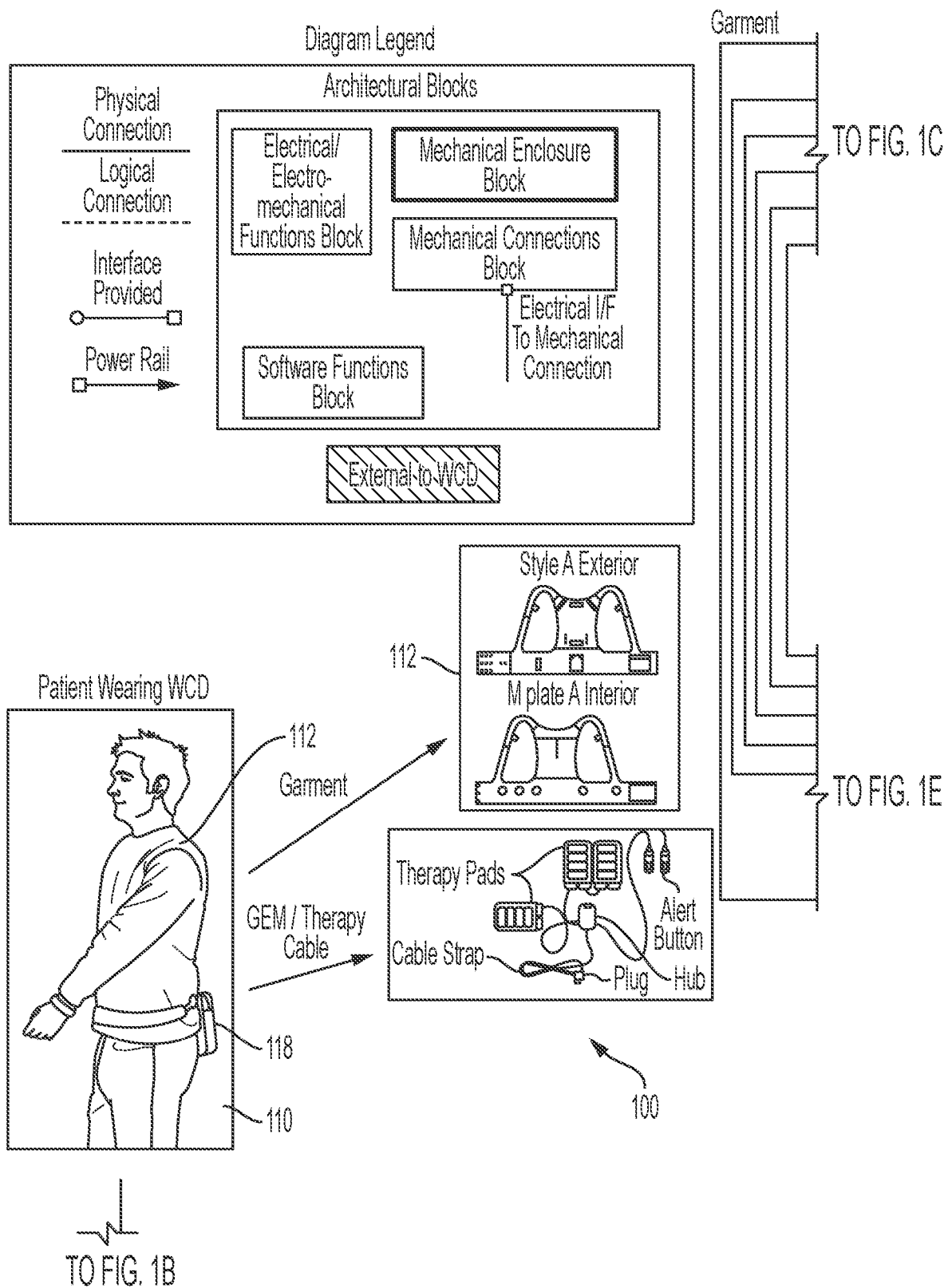
Figure 1B:
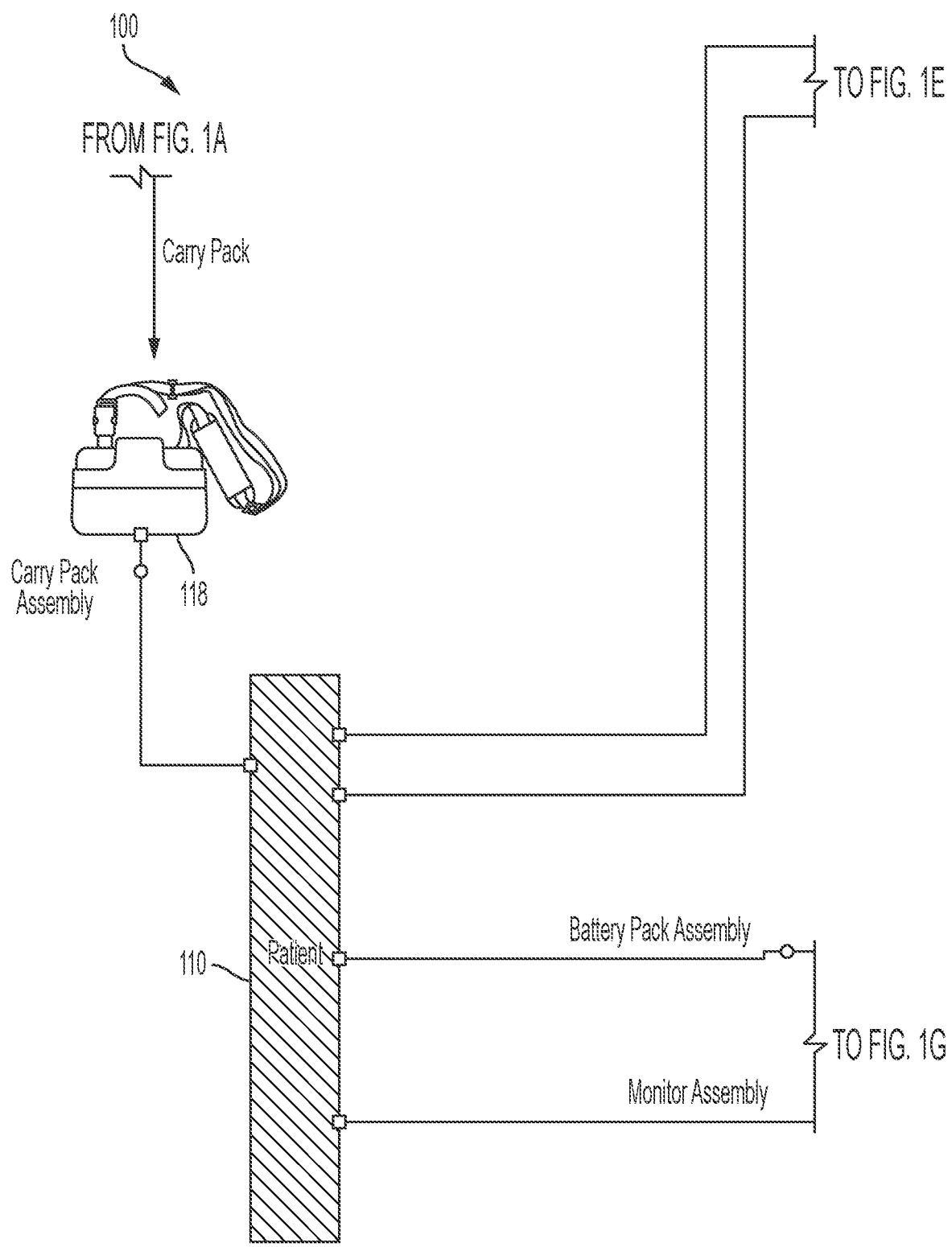

It will be appreciated that for simplicity and/or clarity of illustration, elements illustrated in the figures have not necessarily been drawn to scale. For example, the dimensions of some of the elements may be exaggerated relative to other elements for clarity. Further, if considered appropriate, reference numerals have been repeated among the figures to indicate corresponding and/or analogous elements.

DETAILED DESCRIPTION

In the following detailed description, numerous specific details are set forth to provide a thorough understanding of claimed subject matter. It will, however, be understood by those skilled in the art that claimed subject matter may be practiced without these specific details. In other instances, well-known methods, procedures, components and/or circuits have not been described in detail.

In the following description and/or claims, the terms coupled and/or connected, along with their derivatives, may be used. In particular embodiments, connected may be used to indicate that two or more elements are in direct physical and/or electrical contact with each other. Coupled may mean that two or more elements are in direct physical and/or electrical contact. However, coupled may also mean that two or more elements may not be in direct contact with each other, but yet may still cooperate and/or interact with each other. For example, "coupled" may mean that two or more elements do not contact each other but are indirectly joined together via another element or intermediate elements. Finally, the terms "on," "overlying," and "over" may be used in the following description and claims. "On," "overlying," and "over" may be used to indicate that two or more elements are in direct physical contact with each other. It should be noted, however, that "over" may also mean that two or more elements are not in direct contact with each other. For example, "over" may mean that one element is above another element but not contact each other and may have another element or elements in between the two elements. Furthermore, the term "and/or" may mean "and", it may mean "or", it may mean "exclusive-or", it may mean "one", it may mean "some, but not all", it may mean "neither", and/or it may mean "both", although the scope of claimed subject matter is not limited in this respect. In the following description and/or claims, the terms "comprise" and "include," along with their derivatives, may be used and are intended as synonyms for each other.

Referring now to FIG. 1A through FIG. 1H, a diagram of a wearable cardioverter defibrillator (WCD) in accordance with one or more embodiments will be discussed. A wearable cardioverter defibrillator (WCD) 100 according to embodiments may protect an ambulatory patient by electrically restarting his or her heart if needed. Such a WCD 100 may have a number of components. These components can be provided separately as modules that can be interconnected, or can be combined with other components, and so on.

FIG. 1A depicts a patient 110. Patient 110 may also be referred to as a person and/or wearer since the patient is wearing components of the WCD 100. Patient 110 can be ambulatory, which means that, while wearing the wearable portion of the WCD 100, patient 110 can walk around and is not necessarily bed-ridden. While patient 110 may be considered to be also a "user" of the WCD 100, this is not a requirement. For instance, a user of the wearable cardioverter defibrillator (WCD) 100 also may be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD 100 according to embodiments can be configured to defibrillate the patient 110 who is wearing and/or carrying the designated parts of the WCD 100. Defibrillating can be by the WCD 100 delivering an electrical charge to the patient's body in the form of an electric shock. The electric shock can be delivered in one or more pulses.

In particular, FIG. 1A through FIG. 1H also depict components of a WCD 100 made according to embodiments. One such component is a support structure or garment 112 that is wearable by ambulatory patient 110. Accordingly, support structure 112 is configured to be worn by ambulatory patient 110 for at least several hours per day, and for at least several days, even a few months. It will be understood that support structure 112 is shown only generically in FIG. 1A through FIG. 1H, and in fact partly conceptually. FIG. 1A through FIG. 1H are provided merely to illustrate concepts about support structure 112 and are not to be construed as limiting how support structure 112 is implemented, or how it is worn.

Support structure 112 can be implemented in many different ways. For example, it can be implemented in a single component or a combination of multiple components. In embodiments, support structure 112 could include a vest, a half-vest, a garment, etc. In such embodiments such items can be worn similarly to analogous articles of clothing. In embodiments, support structure 112 could include a harness, one or more belts or straps, etc. In such embodiments, such items can be worn by the patient 110 around the torso, hips, over the shoulder, etc. In embodiments, support structure 112 can include a container or housing, which even can be waterproof. In such embodiments, the support structure 112 can be worn by being attached to the patient's body by adhesive material, for example as shown and described in U.S. Pat. No. 8,024,037 which is incorporated herein by reference in its entirety. Support structure 112 can even be implemented as described for the support structure of US Pat. App. No. US2017/0056682 which is incorporated herein by reference in its entirety. In such embodiments, the person skilled in the art will recognize that additional components of the WCD 100 can be in the housing of a support structure 112 instead of being attached externally to the support structure 112, for example as described in the US2017/0056682 document. There can be other examples.

FIG. 1E, FIG. 1F, FIG. 1G, and FIG. 1H show a sample external defibrillator 100 comprising a monitor 116, also referred to as a Personal Electrocardiogram (ECG) Monitor (PEM) and a hub 114. In some embodiments, most of the operational circuitry and the energy providing components of WCD 100 may reside within monitor 116 which in turn may couple to support structure 112 via hub 114 which serves to route signals, power, and shock delivery between the patient 110 and monitor 116 via hub 114. In some embodiments, monitor 116 may be contained in a housing such as a carry pack assembly 118 (FIG. 1A and FIG. 1B) carried or worn by the patient 110, and hub 114 may be attached to support structure 112, although the scope of the present subject matter is not limited in this respect. As described in more detail later in this document, some aspects of WCD 100 include a housing and an energy storage module within the housing. As such, in the context of a WCD 100, monitor 116 is sometimes called a main electronics module. The energy storage module in monitor 116 can be configured to store an electrical charge. Other components can cause at least some of the stored electrical charge to be discharged via electrodes through the patient 110 so as to deliver one or more defibrillation shocks through the patient 110.

Figure 1C:
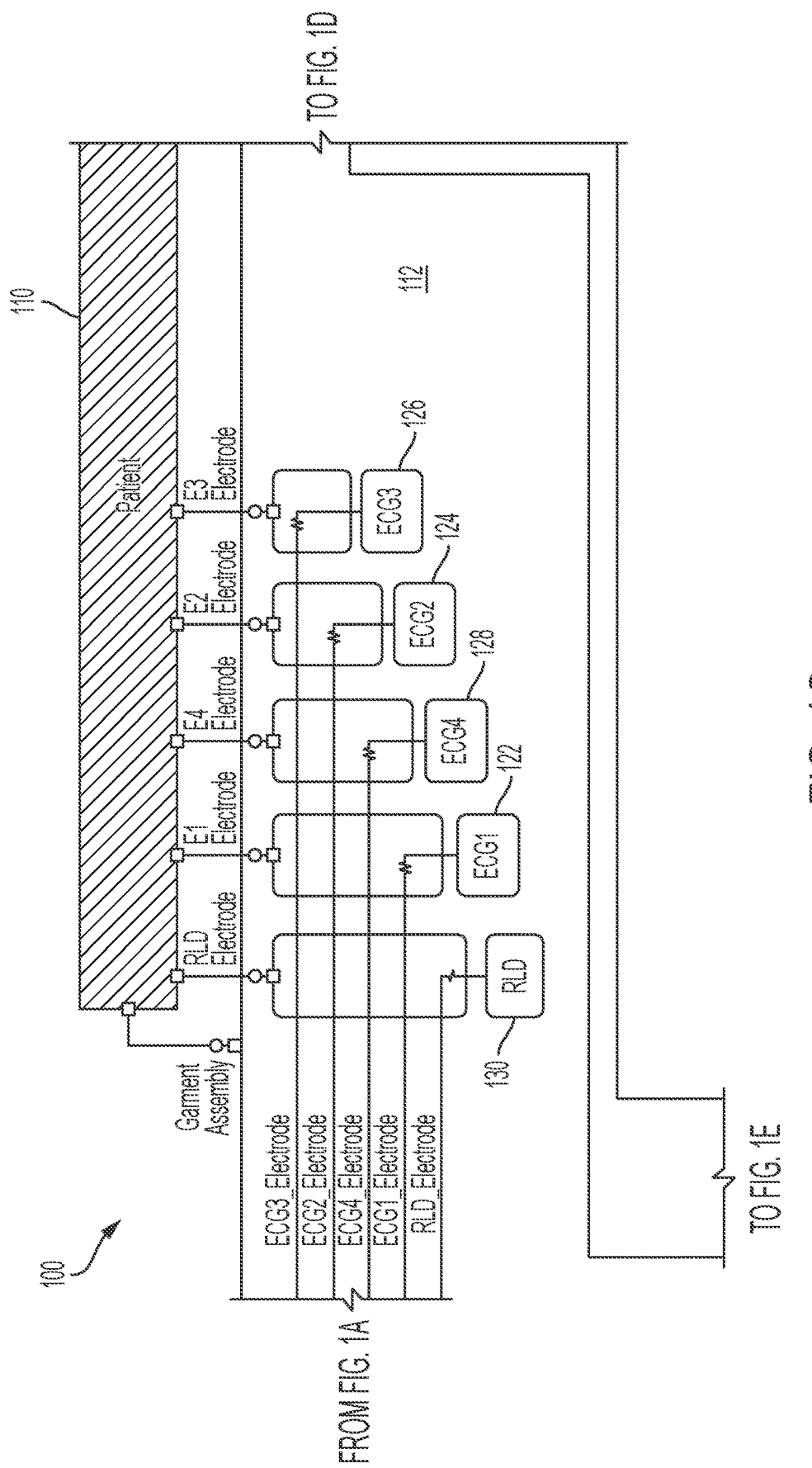
Figure 1D:
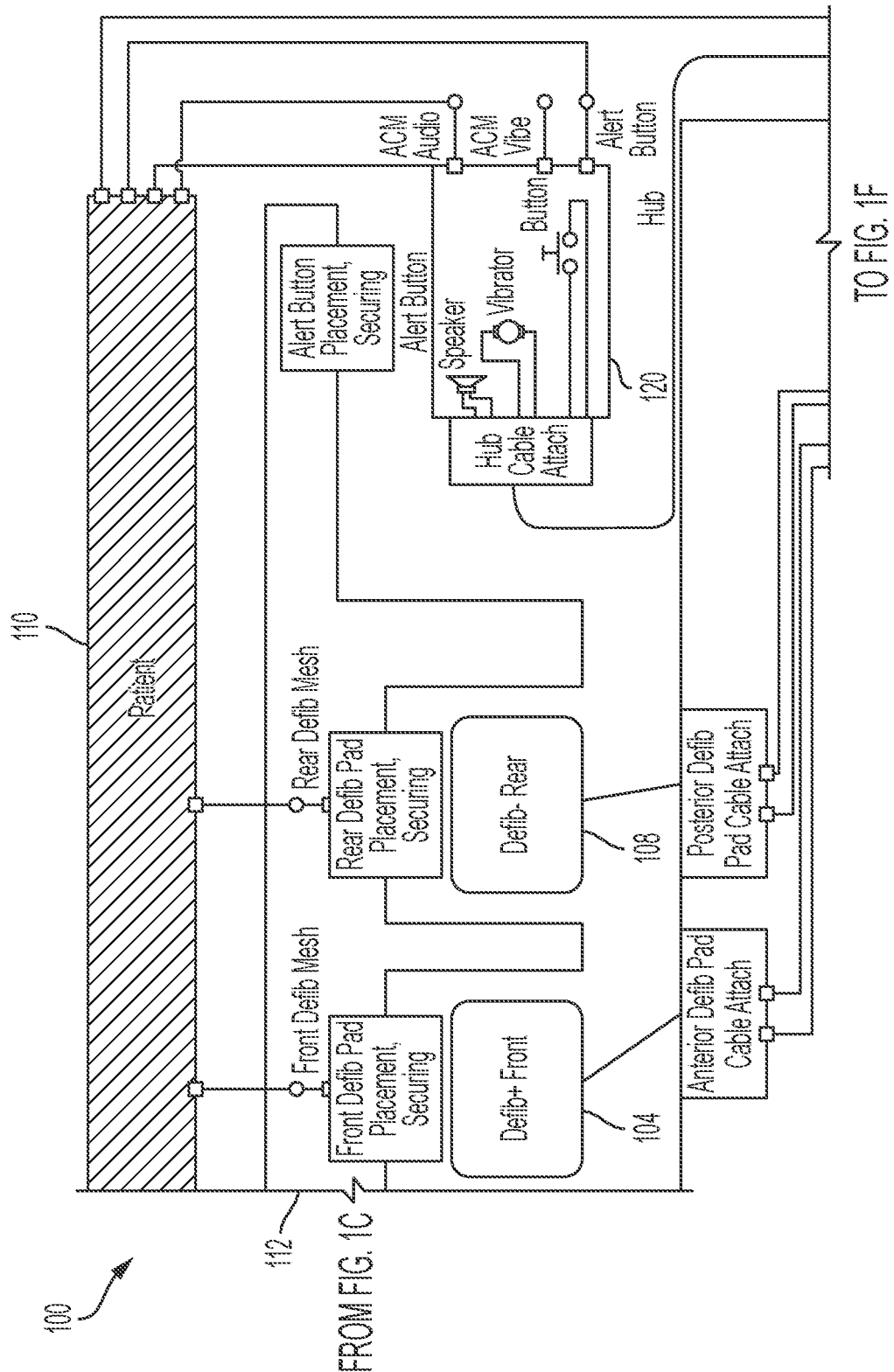

FIG. 1D shows sample defibrillation electrodes such as electrode 104 and electrode 108 which are coupled to monitor 116 via hub 114 via electrode leads. Defibrillation electrodes 104 and 108 can be configured to be worn by patient 110 in a number of ways. For instance, monitor 116 and defibrillation electrodes 104 and 108 can be coupled to support structure 112 either directly or indirectly. In other words, support structure 112 can be configured to be worn by ambulatory patient 110 so as to maintain at least one of electrodes 104 and 108 on the body of ambulatory patient 110 while patient 110 is moving around, etc. The electrode can be thus maintained on the body of the patient 110 by being attached to the skin of patient 110, simply pressed against the skin directly or through garments, etc. In some embodiments the electrode is not necessarily pressed against the skin but becomes biased that way upon sensing a condition that could merit intervention by the WCD 100. In addition, many of the components of monitor 116 can be considered coupled to support structure 112 either directly or indirectly via at least one of defibrillation electrodes 104 or 108.

When defibrillation electrodes 104 and 108 make good electrical contact with the body of patient 110, monitor 116 can administer, via electrodes 104 and 108, a brief, strong electric pulse through the body of the patient 110. Such a pulse is also known as shock, defibrillation shock, therapy, electrotherapy, therapy shock, etc. The pulse is intended to go through and restart the heart of the patient 110 in an effort to save the life of the patient 110. The pulse further can include one or more pacing pulses of lesser magnitude to simply pace the patient's heart if needed, and so on.

Some prior defibrillators may decide whether to defibrillate or not based on an electrocardiogram (ECG) signal of the patient 110. Monitor 116, however, may initiate defibrillation or hold-off defibrillation based on a variety of inputs with the ECG signal merely being one of these inputs, and the scope of the disclosed subject matter is not limited in this respect.

The WCD 100 according to embodiments can obtain data from patient 110. For collecting such data, the WCD 100 optionally may include an outside monitoring device (not shown) external to monitor 116. Such a device may be called an "outside" device because it could be provided as a standalone device, for example not within the housing of monitor 116. An outside monitoring device can be configured to sense or monitor at least one local parameter. A local parameter can be a parameter of patient 110, a parameter of the WCD 100, or a parameter of the environment, as will be described later in this document.

For some of these parameters, an outside monitoring device may include one or more sensors or transducers. Each one of such sensors can be configured to sense a parameter of patient 110, and to render an input responsive to the sensed parameter. In some embodiments the input is quantitative, such as values of a sensed parameter. In other embodiments the input is qualitative, such as informing whether or not a threshold is crossed, and so on. Sometimes these inputs about patient 110 are also called physiological inputs and patient inputs. In embodiments, a sensor can be construed more broadly, as encompassing many individual sensors.

Optionally, an outside monitoring device can be physically coupled to support structure 112. In addition, an outside monitoring device may be communicatively coupled with other components that are coupled to support structure 112. Such communication can be implemented by a communication module, as will be deemed applicable by a person skilled in the art in view of this description.

In some embodiments, one or more of the components of the shown WCD 100 may be customized for patient 110. This customization may include a number of aspects. For instance, support structure 112 can be fitted to the body of patient 110. For another instance, baseline physiological parameters of patient 110 can be measured, such as the heart rate of patient 110 while resting, while walking, motion detector outputs while walking, etc. The measured values of such baseline physiological parameters can be used to customize the WCD 100 in order to make its diagnoses more accurate, since patients' bodies differ from one another. Of course, such parameter values can be stored in a memory of the WCD 100, and so on. Moreover, a programming interface can be made according to embodiments, which receives such measured values of baseline physiological parameters. Such a programming interface may input automatically in the WCD 100 these, along with other data.

Figure 1E:
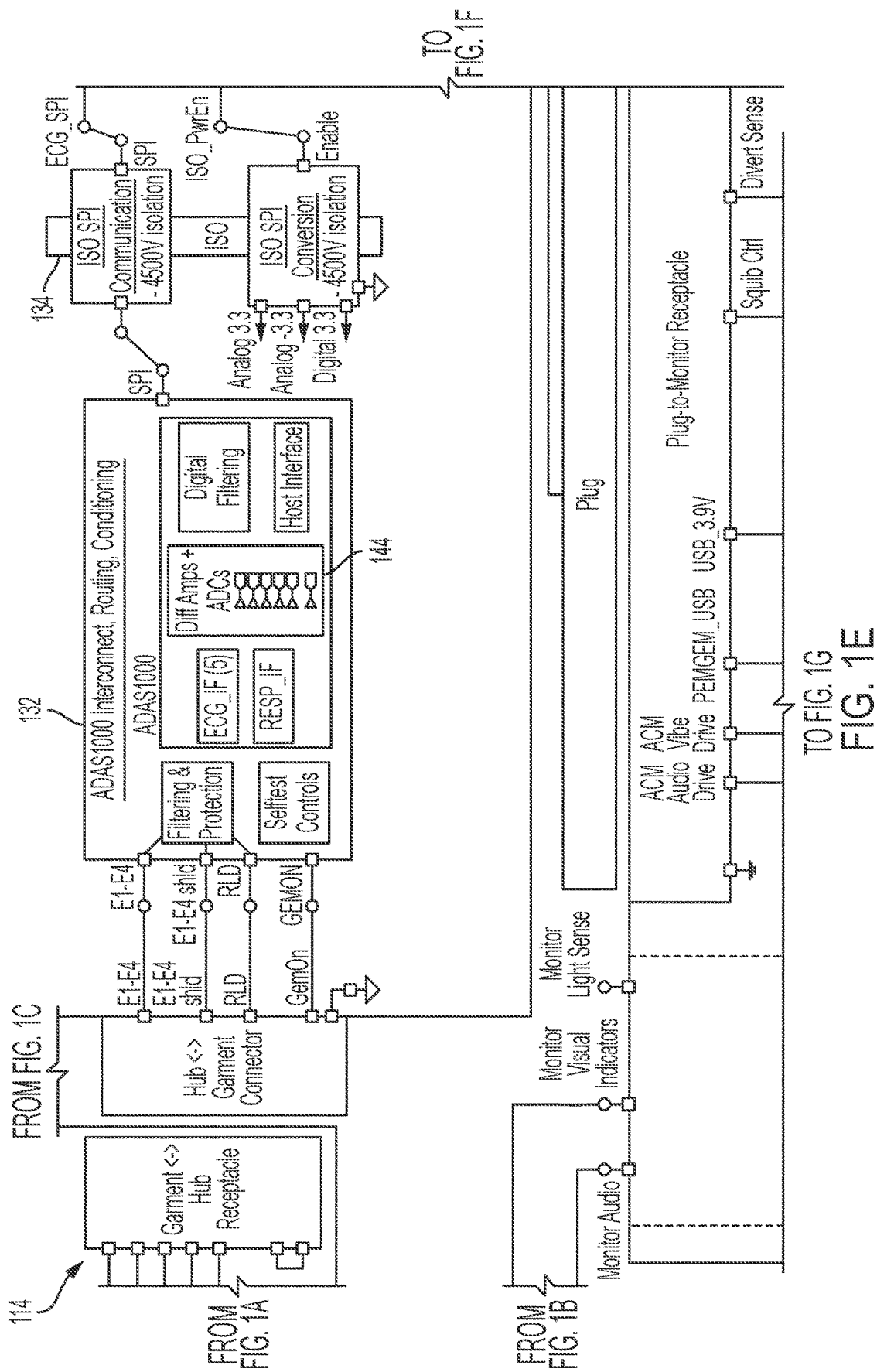
Figure 1F:
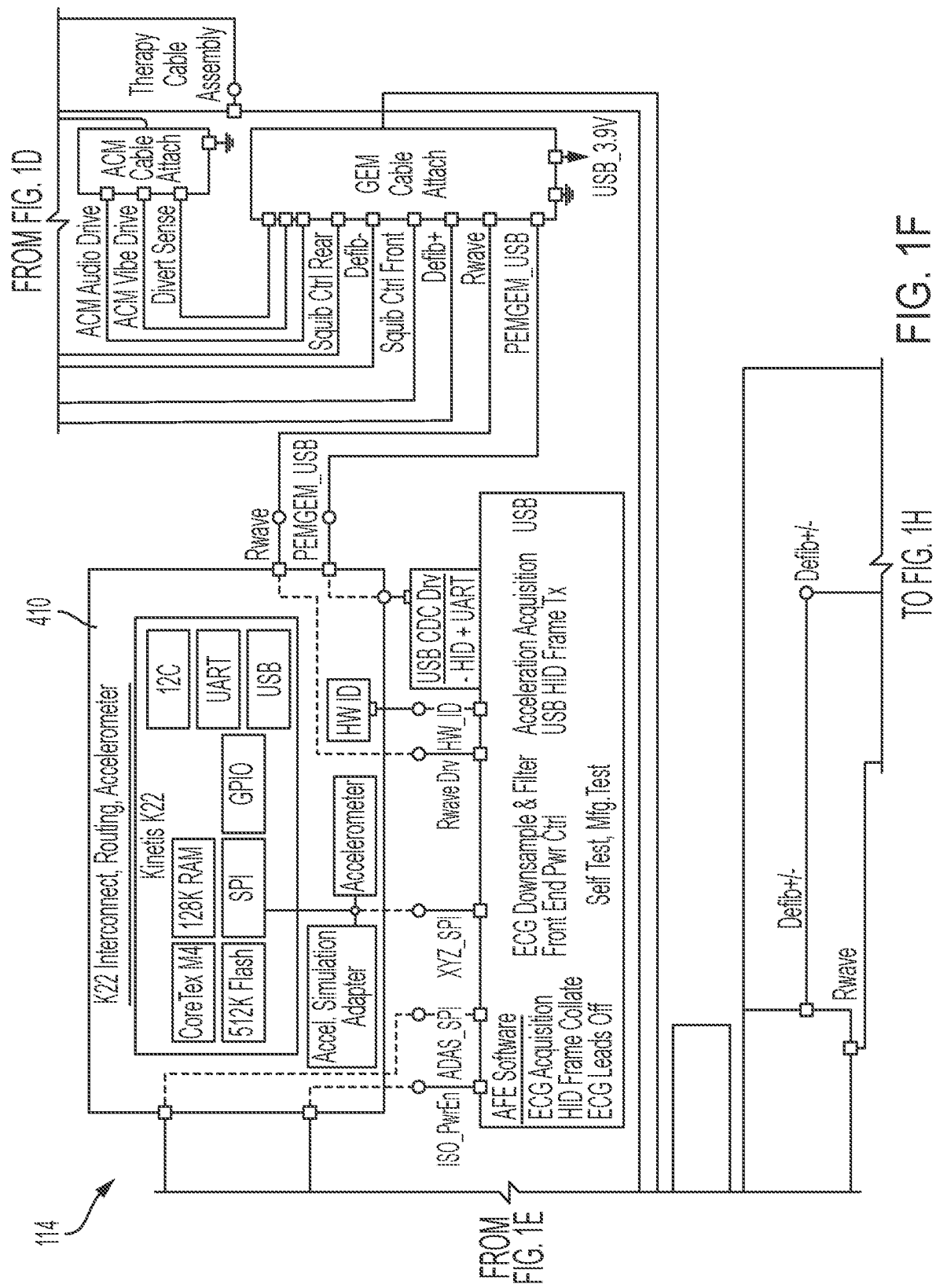
Figure 1G:
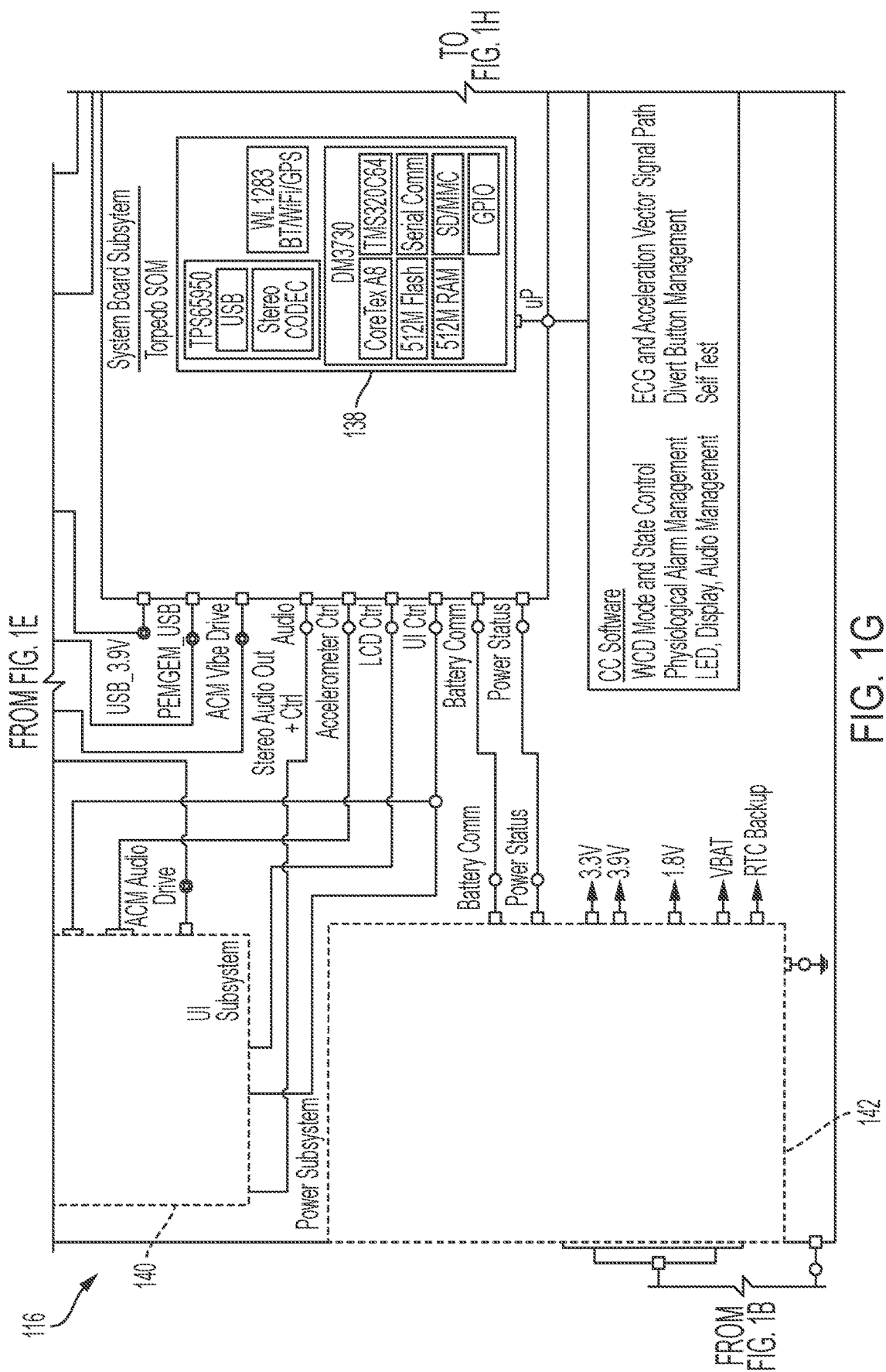

In one or more embodiments, for example as shown in FIG. 1C, WCD 100 may comprise the following architecture. Support structure 112 can comprise a garment such as a vest to be worn by the patient 110. Support structure 112 can include ECG electrodes such as electrode (ECG1) 122, electrode (ECG2) 124, electrode (ECG3) 126, and electrode (ECG4) 128, and right-leg drive (RLD) electrode 130. The ECG and RLD electrodes and defibrillation electrodes 104 and 108 can connect to hub 114 which includes front end electronics, interconnects, conditioning, and routing for the electrodes. Hub 114 can be attached to the support structure (vest or garment) 112 on the back of the support structure 112 so that the hub 114 is positioned on the patient's back when the patient 110 is wearing the garment. The circuitry of hub 114, for example as shown in FIG. 1E and FIG. 1F, includes an ECG acquisition system which uses five communication lines E1_ECG, E2_ECG, E3_ECG, E4_ECG, and RLD to connect to the ECG electrodes 122-128 including the RLD electrode 130 of support structure 112. The ECG electrodes connect to the patient's skin to obtain ECG signals from the patient 110. In addition, there are four shield lines and a cable sense line. Hub 114 can include a preamplifier 132 and an isolation barrier 134 which will be discussed in more detail with respect to FIG. 4A and FIG. 4B, below.

An alert button 120 can connect to hub 114 and may include a speaker and vibrator. In addition, alert button 120 can include a button to allow the patient 110 to divert or abort a defibrillator shock in the event the patient 110 believes an impending shock to be unnecessary. Alert button 120 can also be referred to as a stop button, a divert button, or a user interface, and the scope of the disclosed subject matter is not limited in this respect. Hub 114 can connect the electrodes of support structure 112 and the alert button 120 to monitor 116 which houses the main electronics and other components of WCD 100, which may be contained within a carry pack assembly 118 that may be carried by the patient 110 or worn on the patient's hip. Monitor 116 may include the battery 142, the defibrillator capacitor 136, user interface 140, and main processor 138 of WCD 100.

In some embodiments, the processor 138 is a TORPEDO System on Module (SOM) available from Logic PD, Inc. of Eden Prairie, Minn., USA, although the scope of the disclosed subject matter is not limited in this respect. Processor 138 is used to run some portions of the shock decision algorithm to determine when WCD 100 should apply a shock to the patient 110 and is capable of applying filters on four channels simultaneously while also controlling wireless communications and other functions of WCD 100. In some embodiments, at least some portions of the shock algorithm may be run by a controller or processor 410 located in the hub 114 as shown in and described with respect to FIG. 4A and FIG. 4B, below, and the scope of the disclosed subject matter is not limited in this respect. One example portion of the shock algorithm that can be executed by the processor 410 in the hub 144 is the gatekeeper function 612 as shown in and described with respect to FIG. 6 below, and the scope of the disclosed subject matter is not limited in this respect. Monitor 116 also may include a user interface (UI) 140 to allow a user to control and interact with WCD 100. In some embodiments, the user may stop or divert an impending shock via the user interface 140, or via the alert button 120. Monitor 116 also includes a speaker that provides audible alerts and some status indicators.

Figure 2A:
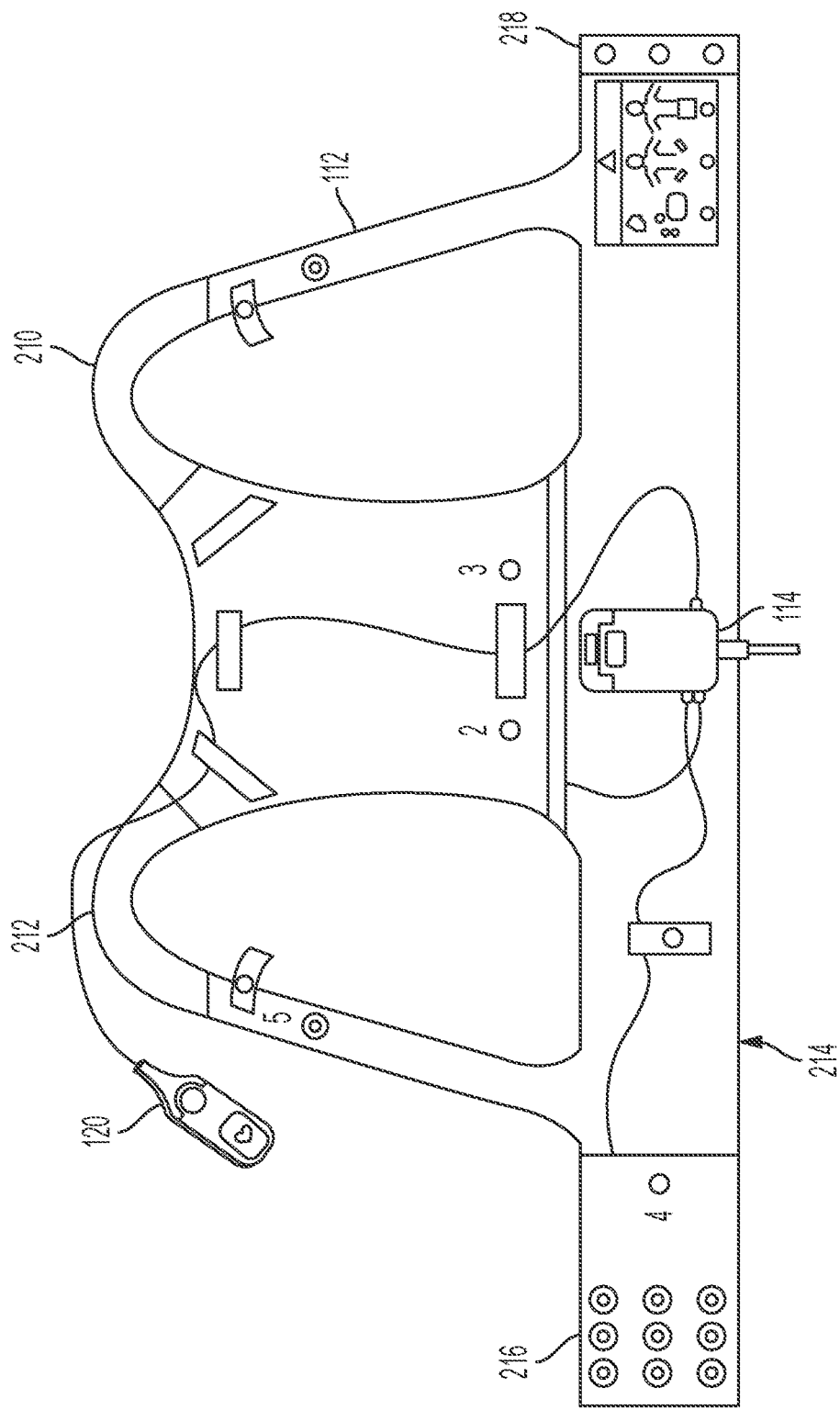
FIG. 2A is a diagram of a back view of a garment of a WCD in accordance with one or more embodiments.

Referring now to FIG. 2A, a diagram of a back view of a garment of a WCD in accordance with one or more embodiments will be discussed. The garment shown in FIG. 2A comprises the support structure 112 of FIG. 1A, FIG. 1C, and FIGS. 1D and 1s shown in a vest configuration. The garment may include shoulder straps 210 and 212 to be placed over the shoulders of the patient 110 and for support of the support structure 112. The garment may include a belt portion 214 to be fastened around the waist of the patient 110. The belt portion 214 may include various fasteners 216 and 218, for example closure snaps, to allow the garment to be fitted to different sized users. Hub 114 can be attached to the back side of the garment, for example on or near the belt portion 214, to allow various cables to be connected to hub 114 including alert button (divert button) 120 and cabling to connect to the therapy/defibrillator electrodes and ECG electrodes (not shown). In some embodiments, support structure 112 can comprise a vest-like fabric garment to be worn on the patient's body underneath an outer shirt or other clothing to allow the electrodes to contact the patient's skin and hold the electrodes in close proximity to and/or direct contact with the patient's skin. Such an arrangement allows for the WCD 100 to obtain ECG signals from the patient and to allow the shock to be applied to the patient 110 when appropriate.

Figure 2B:
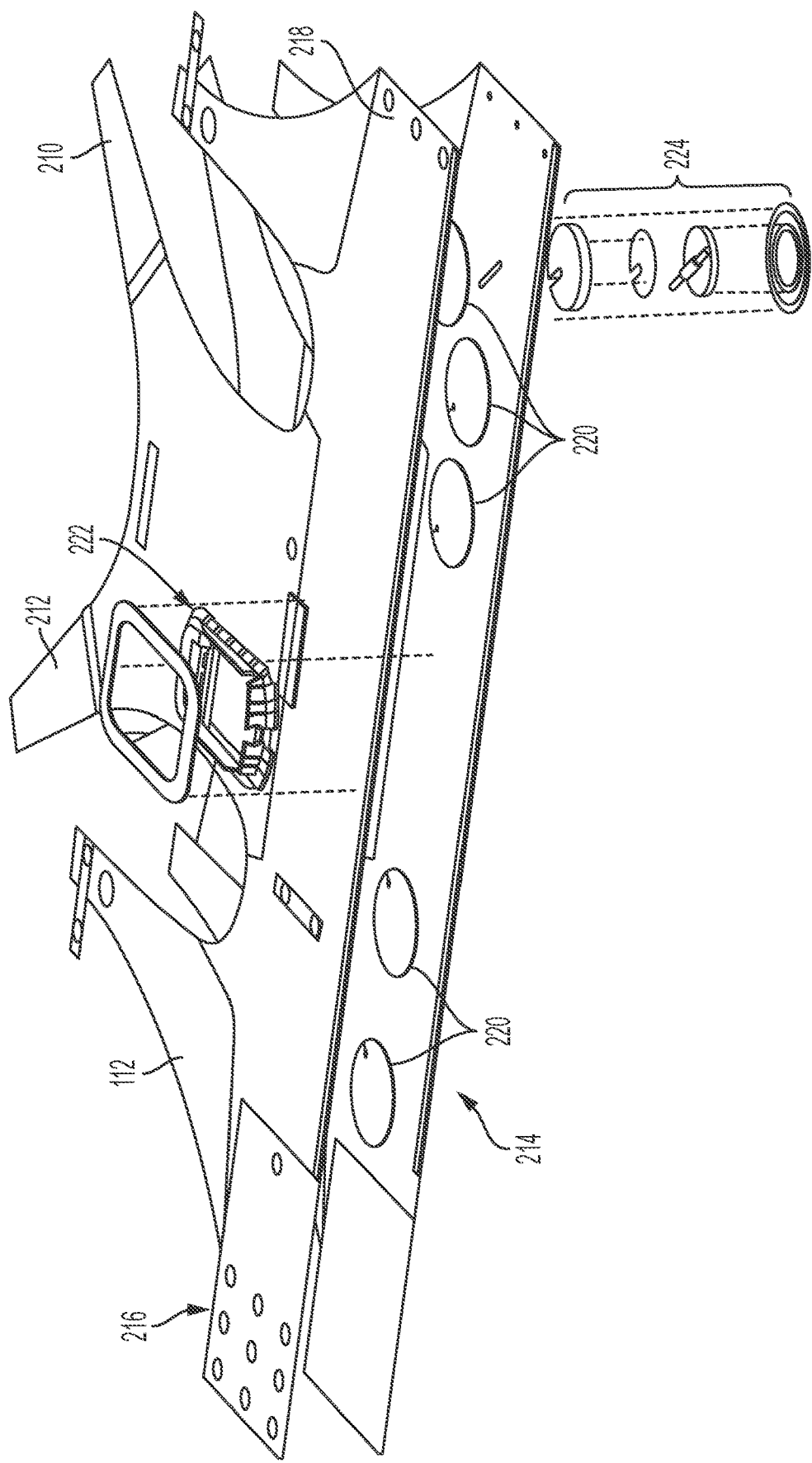
FIG. 2B is a diagram of an exploded view of the garment of a WCD in accordance with one or more embodiments.

Referring now to FIG. 2B, a diagram of an exploded view of the garment of a WCD in accordance with one or more embodiments will be discussed. As discussed with respect to FIG. 2A, above, support structure 112 can comprise a garment made of a soft, stretchy fabric that conforms to the patient's body. Multiple sets of closure mechanisms or fasteners 216 and 218 may comprise, for example, nine fastening structures on one side of belt portion 214 to selectively mate or couple with three fastening structures on another side of belt portion 214 on an outer layer of the garment as to allow the tightness or fit of the garment to be adjusted to the size of the patient 110. The shoulder straps 210 and 212 can be adjustable as well.

The ECG electrodes can comprise structures 220 integrated into the garment so as to be firmly retained. Wiring from the electrodes 220 to a hub connector 222 can be internal to the garment, for example disposed between the layers of the garment. FIG. 2A shows an exploded view 224 of one of the electrodes 220 which is shown in and described in further detail with respect to FIG. 3, below. In some embodiments, hub 114 as shown in FIG. 2A can snap of fit into the hub connector 222 shown in FIG. 2B to make connections between the electronics of the hub 114 and the patient 110. Embodiments of the garment are disclosed in U.S. patent application Ser. No. 15/889,040 filed Feb. 5, 2018 which is incorporated herein by reference in its entirety.

Figure 3:
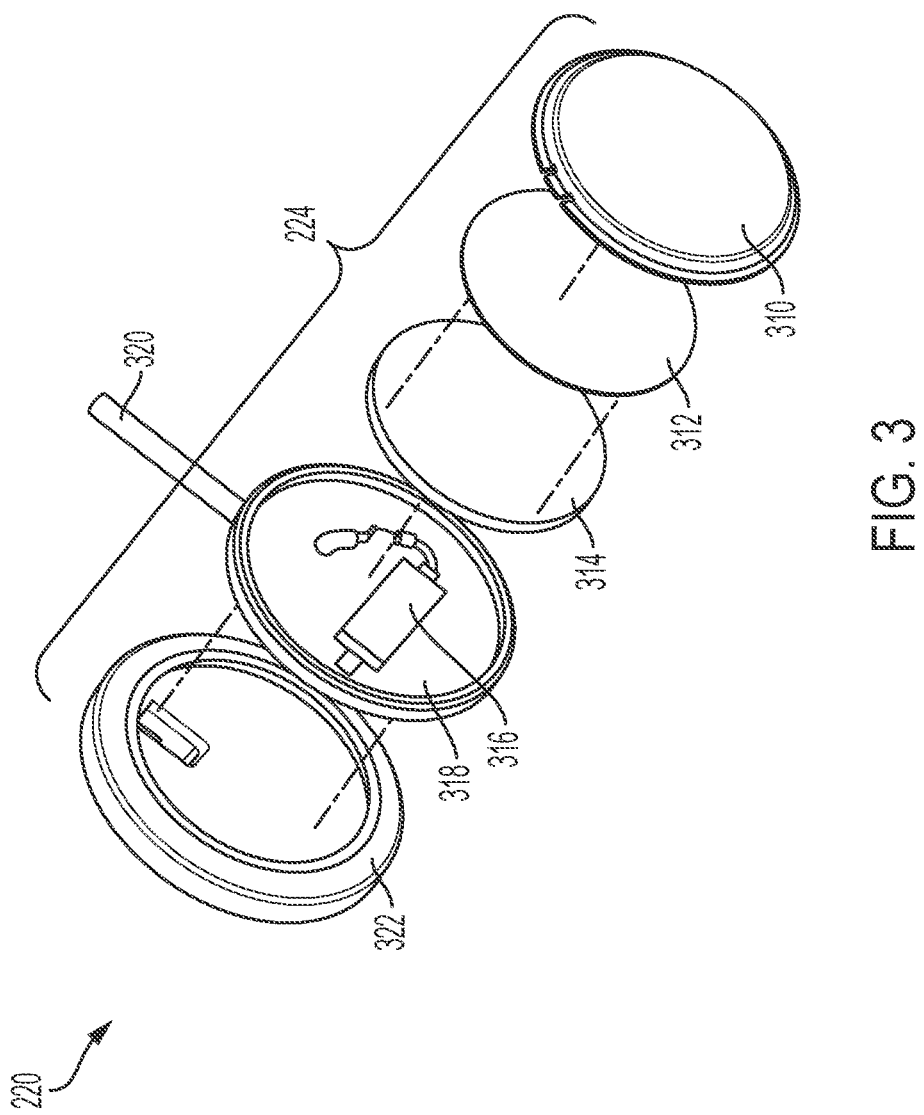
FIG. 3 is a diagram of an electrocardiogram (ECG) electrode used in a WCD in accordance with one or more embodiments.

Referring now to FIG. 3, a diagram of an electrocardiogram (ECG) electrode used in a WCD in accordance with one or more embodiments will be discussed. FIG. 3 illustrates an exploded view of one of the ECG electrodes 220 shown in FIG. 2A, above. In one or more embodiments, the ECG electrodes 220 can comprise a solid silver metal disk electrode such as disk 310 that is resistive rather than capacitive. The disk 310 of the ECG electrode 220 can be silver plated copper on its face. ECG electrode 220 can include a printed circuit board assembly (PCBA) 318 including a resistor 316 wherein the back of the PCBA 318 includes a ground plane that provides electromagnetic shielding for the electrode 220. The ECG cable 320 can be shielded as well in some embodiments. The assembly 224 of the ECG electrode 220 can further include a polyimide structure 312, a premold structure 314, and an overmold structure 322 to form the back side of the ECG electrodes 220.

In embodiments, the ECG electrodes 220 are "dry" electrodes in that they are placed in direct contact against the skin with no gel or electrolyte on the surface of the electrode disk 310 or the patient's skin. The solid metal face of the electrode disk 310 is non-breathable and traps moisture against the skin. In some embodiments such moisture can enhance pickup of the ECG signal.

It should be noted that a capacitive electrode system may be able to pick up an ECG signal without moisture at the electrode-skin interface. Such capacitive electrodes, however, may be more subject to noise pickup because any motion that modulates the electrode-skin capacitance is readily converted to ECG artifacts that can alter the ECG signal and interfere with ECG analysis. The resistive property of the ECG electrode 220 is less susceptible to such ECG artifacts to help reduce the likelihood of a false or unnecessary shock event. Furthermore, although adhesive electrodes may contain an electrolyte that facilitates ECG signal pickup, adhesive electrodes need to be replaced periodically, and the electrolyte may dry out over time and become more susceptible to interfering with proper ECG analysis.

Figure 4A:
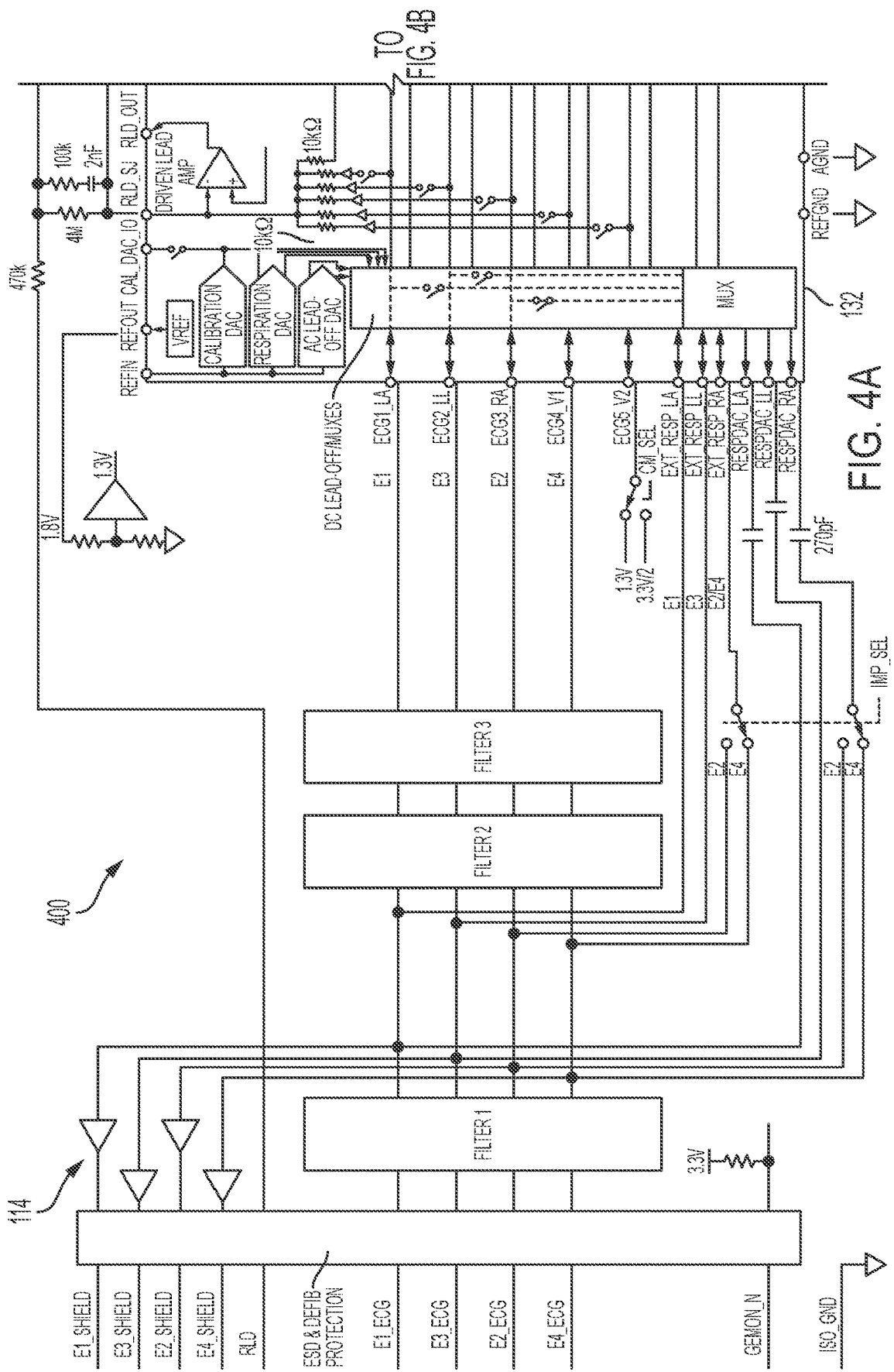
FIG. 4A and FIG. 4B illustrate a diagram of a front end of an ECG device used in a WCD in accordance with one or more embodiments.
Figure 4B:
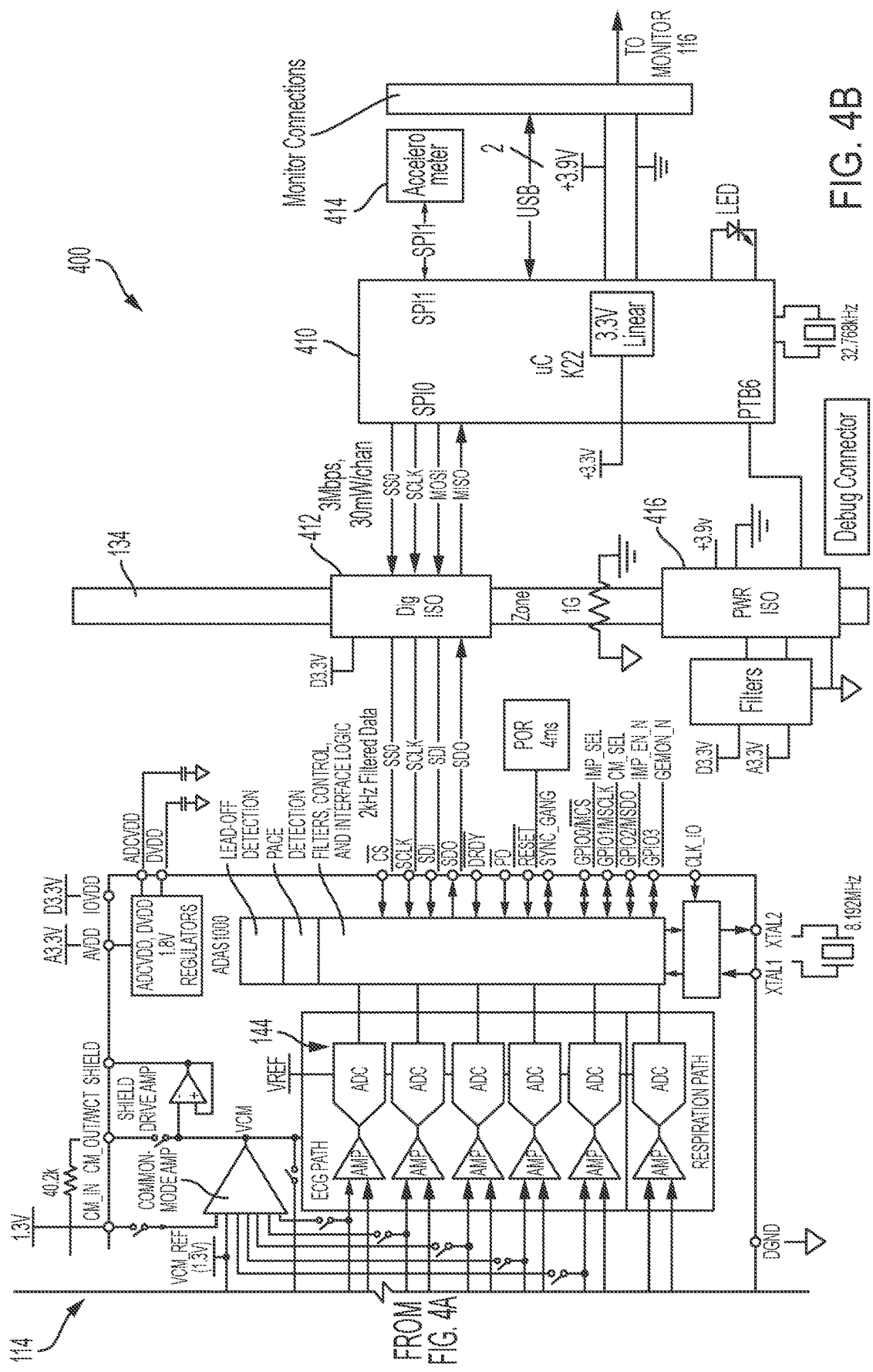

Referring now to FIG. 4A and FIG. 4B, a diagram of a front end of an ECG device used in a WCD in accordance with one or more embodiments will be discussed. The ECG front end circuitry 400 in the hub 114 comprises a preamplifier 132 that is isolated from processor 410 via an isolation barrier 134. In some embodiments, preamplifier 132 can comprise an ADAS1000 preamplifier available from Analog Devices, Inc. of Norwood, Mass., USA, and processor 410 can comprise a KINETIS K22 microcontroller available from NXP Semiconductors N.V. of Eindhoven, The Netherlands, although the scope of the disclosed subject matter is not limited in this respect.

Isolation barrier 134 serves to isolate the preamplifier from processor 410 and the rest of the WCD 100 system. Signals from the ECG electrodes are provided to the preamplifier 132 which converts the ECG signals into digital signals using analog-to-digital converters (ADCs) 144. The digital signals are passed from the preamplifier 132 through the isolation barrier 134 to processor 410 through digital isolator 412. The processor 410 has a Universal Serial Bus (USB) interface that goes to the monitor 116 and the rest of the WCD 100 system. The isolation barrier 134 can also include a power isolator 416 to isolate the power provided to the preamplifier 132 from the power provided to the processor 410.

In some embodiments, ECG front end circuitry 400 includes an isolation barrier configured to electrically isolate preamplifier 132 from the main circuit ground to which other circuits of WCD 100 are connected, for example the circuitry of monitor 116. Isolation barrier 134 may in turn include an additional circuit ground isolated from the main circuit ground. This isolation enhances the quality of the acquired ECG data, which may result in fewer false alarms and increased patient safety. Non-isolated ECG acquisition systems are susceptible to environmental noise sources such as 60 Hz fields in the vicinity of the WCD 100. Patient leakage currents could be difficult to control. Further, electrical noise generated by switch mode power supplies or high voltage charging circuits could couple into the ECG acquisition system of the WCD 100. Thus, preamplifier 132 may have its own ground reference which is different from and isolated from the ground reference used by processor 410 and the remaining circuits of the WCD 100 including the circuits of monitor 116.

In one or more embodiments, isolation barrier 134 can include digital isolator 412 and power isolator 416. Digital isolator 412 can comprise any one or more types of isolators such as galvanic couplers, such as provided by inductance or capacitance devices, such as an isolation transformer or an isolation capacitor, or by a non-electrical means, such as an opto-isolator comprising for example photodiodes and/or phototransistors, and the scope of the disclosed subject matter is not limited in this respect. In some embodiments, the isolation barrier 134 provides protection from the voltages applied by the defibrillator discharge circuit provided by monitor 116. Power isolator 416 can be configured to transfer power across the isolation barrier 134 without providing DC coupling across the isolation barrier 134, for example using a transformer, although the scope of the disclosed subject matter is not limited in this respect.

In one or more embodiments, the preamplifier 132 has four single-ended ECG inputs receiving the ECG signals, an active right-leg drive, a wide dynamic range, and direct-current (DC) leads-off detection. In some embodiments, preamplifier 132 supports DC leads-off detection, and in other embodiments preamplifier supports alternating-current (AC) leads-off detection, or both, and the scope of the disclosed subject matter is not limited in this respect. In some embodiments, preamplifier 132 includes circuitry to measure the patient impedance values between the ECG electrodes. These impedance values can be used to detect the patient's respiration, for example as shown in U.S. application Ser. No. 15/792,860 filed Oct. 25, 2017, published as US 2018/0117299 A1, and which is incorporated herein by reference in its entirety. As shown in FIG. 4A, in some embodiments the lines E1_ECG, E2_ECG, E3_ECG, and E4_ECG connect to the ECG electrodes in the garment or support structure 112. The RLD line connects to another electrode that is used as a right-leg drive. The preamplifier 132 digitizes the ECG signals so that digitized values of the ECG signals, not the actual ECG signals, are passed through the isolation barrier 134 to the processor 410. The ECG front end circuitry 400 is all contained in a small module comprising the hub 114 that is attached to the garment or support structure 112, for example in the middle of the patient's back as shown in FIG. 2A. In other embodiments the hub 114 may be attached to various other locations on the garment or support structure 112 other than the middle of the patient's back. For example, the hub 114 may be located at a shoulder area, a side area, or a front or chest area of the patient 110 when the patient 110 is wearing the support structure, and the scope of the disclosed subject matter is not limited in this respect. In some embodiments, ECG front end circuitry 400 also can include a motion sensor 414 such as, for example, a 3-axis accelerometer in the same package comprising the hub 114. In some embodiments, the microprocessor sends the ECG signals, the ECG leads-off signals, and the accelerometer signals over a USB connection to monitor 116 which performs most of the signal processing of the WCD 100. In some embodiments, ECG leads-off is detected by injecting a low-level DC current into each electrode. The return path for this current is through the RLD line. If an electrode becomes disconnected from the patient 110, the current injection causes the DC voltage at the electrode to hit the upper rail. When an electrode voltage hits the rail, it is flagged as being "off."

In one or more embodiments, the isolation barrier 134 shown in FIG. 4B may contribute to the enhanced performance of the WCD system because the isolation barrier 134 operates to greatly enhance the common-mode rejection of the WCD 100. In some embodiments, the preamplifier 132 has an input voltage range of 0 V to 2.6 V. The ground reference is nominally at 1.3 V. Any channel with a DC level of greater than 2.4 V or less than 0.2 V can be considered "off". This arrangement gives the ECG front end circuitry 400 a usable dynamic range of +/−1.1 V, which is relatively large compared to the size of the cardiac signal of interest, which is typically around 1 mV. Such a wide dynamic range allows at least most of the ECG filtering to happen in software without the signal being clipped. Digital filters can be very effective at removing artifacts and may contribute to the enhanced false positive performance of the WCD 100 according to embodiments as described herein.

In some embodiments, the preamplifier 132 has a very high sample rate so the anti-aliasing filters have little impact on the ECG signal quality. The preamplifier 132 is to provide data to the processor 410 at a 2 kHz rate with a bandwidth from DC to 250 Hz. The software down samples to 500 Hz and further bandlimits the signal for algorithm processing. It should be noted that aspects of embodiments of the ECG front end circuitry 400 are disclosed in U.S. application Ser. No. 15/365,801 filed Nov. 30, 2016 which is incorporated herein by reference in its entirety Referring now to FIG. 5, a diagram of four ECG monitoring vectors used in a WCD in accordance with one or more embodiments will be discussed. In some embodiments, all the digitized ECG signals are referenced to the isolated ground of the ECG front end circuitry 400. Differential vectors can be formed by subtracting two digitized ECG signals. ECG rhythm analysis then can be performed on these four vectors. Such differential vectors may include, for example, vector (E24) 510, vector (E34) 512, vector (E1) 514, and vector (E13) 516. The defibrillator shock vector 518 may be generated between the anterior defibrillation pad 104 and the posterior defibrillation pad 108. The ECG analysis algorithm includes provisions for excluding vectors that have noise or when a leads-off condition or situation is detected. Monitoring four vectors rather than monitoring two vectors is believed to contribute to enhanced ECG signal analysis and processing of the shock application algorithm to reduce the number of false shock events.

In one or more embodiments, the signals from four ECG electrodes can be combined to form six different vectors. In some embodiments, WCD 100 uses four vectors for QRS complex analysis and/or heart rate analysis to determine if a shock should be applied. The WCD 100 is also capable of performing the analysis and shock application determination if one or more of the vectors is noisy or one or more of the ECG leads is in a lead-off condition wherein the lead is not contacting the patient's skin or is not sufficiently contacting the patient's skin to allow an ECG signal to be obtained with that ECG lead. In some embodiments, three ECG electrodes may be used and three ECG vectors may be analyzed. In other embodiments, five or six ECG vectors may be analyzed using four ECG electrodes. In some embodiments, a single vector is used and analyzed. It should be noted that in general WCD 100 may use and analyze fewer than four vectors or greater than four vectors, and the number of vectors can be increased beyond six vectors by using additional ECG electrodes, and the scope of the disclosed subject matter is not limited in this respect.

Figure 5:
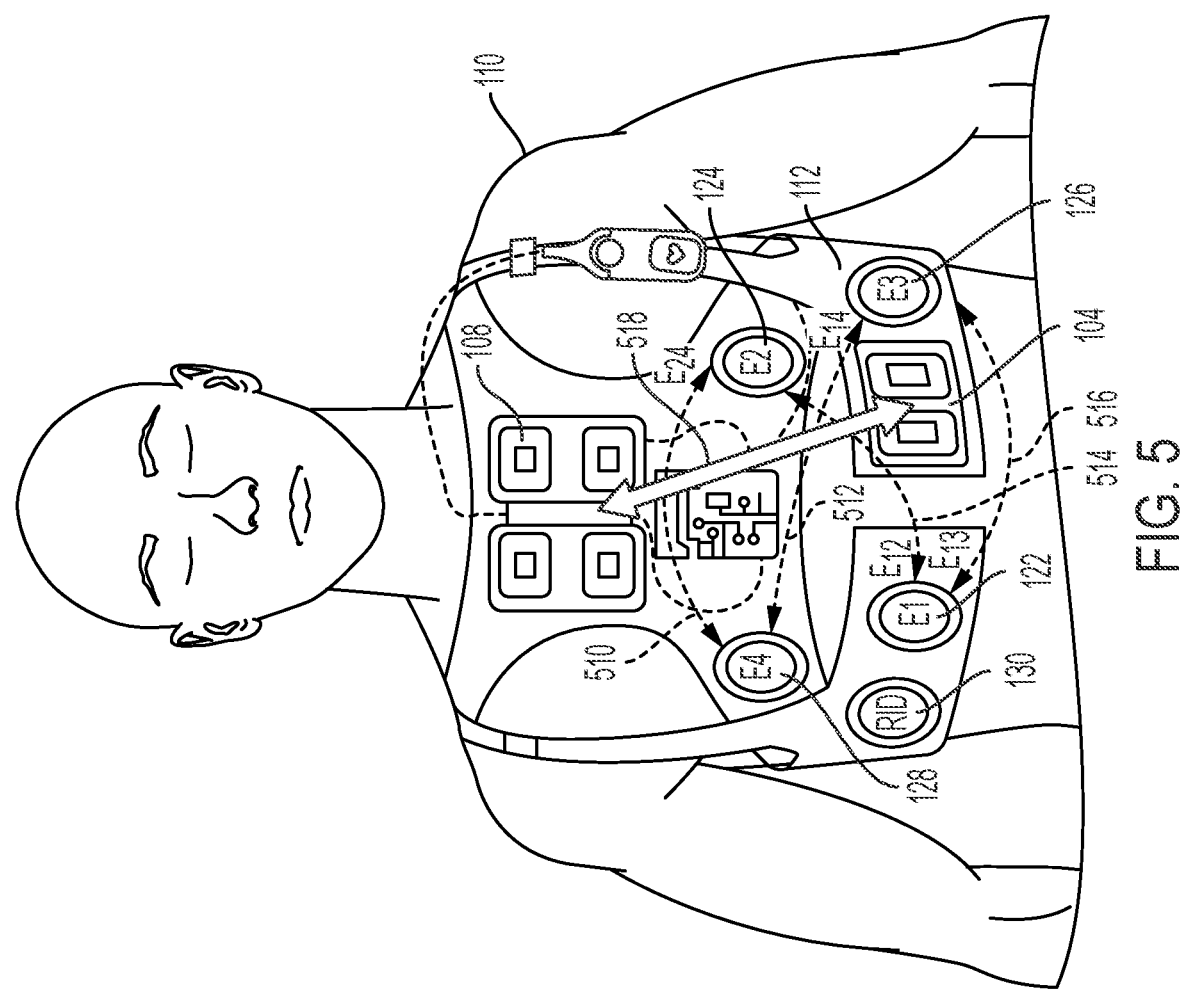
FIG. 5 is a diagram of four ECG monitoring vectors used in a WCD in accordance with one or more embodiments.

In one or more embodiments as shown in FIG. 5, the ECG electrodes are placed circumferentially around the torso of the patient 110 so that the garment or support structure 112 can be used to ensure adequate electrode-skin contact with the patient's skin. It should be noted that other alternative electrode placements may be used, and the scope of the disclosed subject matter is not limited in this respect. For example, adhesive electrode embodiments can provide flexibility in electrode placement in selected locations of the patient's body and may achieve better signal pickup at these selected locations. For example, electrode locations can be selected during a patient-fitting process in which various electrode locations can be changed, and those locations with better or the best ECG signals can be selected, although the scope of the disclosed subject matter is not limited in this respect.

Figure 6:
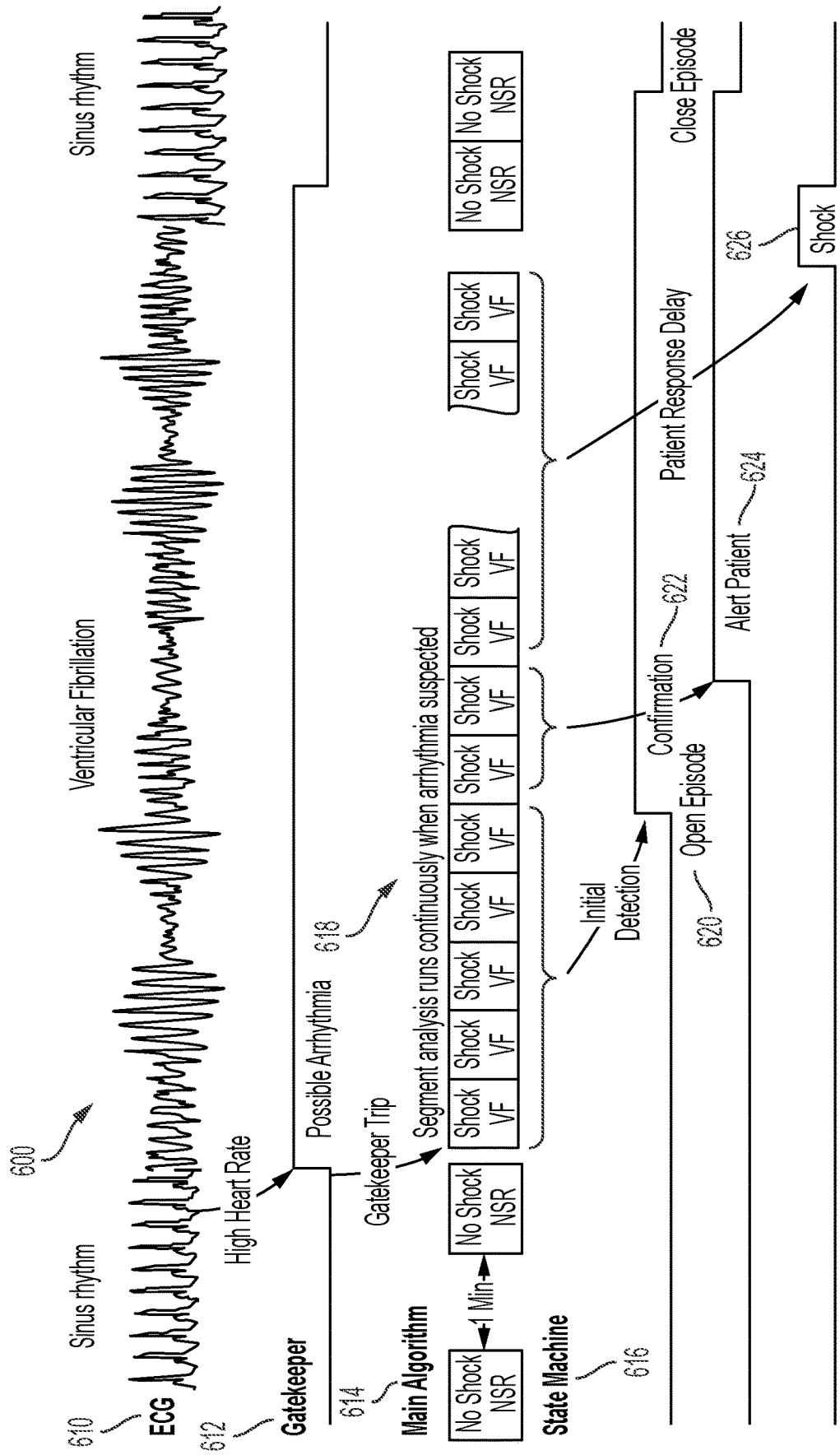
FIG. 6 is a diagram of segment based processing used in a WCD in accordance with one or more embodiments.

Referring now to FIG. 6, a diagram of segment based processing used in a WCD in accordance with one or more embodiments will be discussed. The segment-based processing analysis 600 shown in FIG. 6 is utilized by WCD 100 to make shock/no-shock decisions based at least in part on successive segments of ECG data. The segments can be 4.8 seconds in duration, although the scope of the disclosed subject matter is not limited in this respect.

The WCD 100 monitors and analyzes ECG data 610 to make a shock/no-shock decision. A gatekeeper function 612 may be used to provide an early indication that an arrhythmia may be present in the patient 110. An example embodiment of this gatekeeper functionality is disclosed in U.S. application Ser. No. 15/715,500 filed Sep. 26, 2017 which is incorporated herein by reference in its entirety. In some embodiments, if an arrhythmia is suspected with the gatekeeper function 612, then the main rhythm analysis algorithm 614 is triggered to start analyzing successive segments 618 of ECG data, and a shock/no-shock decision is made for each of the individual segments 618. If a string of the segments 618, for example six segments, provide a shock decision, then an episode is opened (Open Episode) 620 in a state machine 616. In some embodiments, this starts an internal storage of ECG information in a memory of the WCD 100 for later review. After the Open Episode 620, if the shockable rhythm persists for a confirmation period, for example for two or more segments for ventricular fibrillation (VF) or nineteen or more segments for ventricular tachycardia (VT) in some embodiments, then the patient alert sequence (Alert Patient) 624 is initiated. If the patient 110 does not respond within a specified amount of time after initiation of the patient alert sequence, for example after 20 seconds, then a shock (Shock) 626 is delivered to the patient 110.

In a further enhancement in accordance with one or more embodiments, processor 138 is configured to implement the rhythm analysis algorithm 614 to analyze the string of segments to allow for one or more segments of no shock decisions that may, for example, be caused by a false negative decision. In some embodiments, a VF episode is opened when five of six consecutive segments are determined to be shockable for VF, and VF is confirmed if the next two segments are confirmed at VF. In some embodiments, a VT episode is opened when five of six consecutive segments are determined to be shockable for VT, and VT is confirmed when fifteen of nineteen segments are determined to be shockable for VT. In other embodiments, the number of no shock segments that are tolerated in the string can be based on the accuracy of the shock/no shock algorithm. For example, in embodiments in which a very accurate algorithm is used by processor 138, a smaller number of no shock segments could be tolerated to reduce the number of false positive episode opening and/or VT/VF confirmations.

In other embodiments, the strings of consecutive segments may be of different lengths, and the criteria for opening an episode and/or confirming VT or VF can be based on different numbers of segments determined to be shockable. A shorter string for opening an episode may increase sensitivity and reduce specificity. That is, a shorter string for opening an episode may result in more episodes being opened but with an increased risk of false alarms that may lead to unneeded shocks. A longer string, however, may reduce sensitivity and increase specificity, resulting in fewer episodes being opened but the risk of failing to detect VT or VF would increase.

In some embodiments, the number of consecutive segments in a string for opening an episode can be based on time. For example, in some embodiments an episode opening time is selected to be fifteen seconds, but in other embodiments opening different times can be used. A shorter opening time may increase sensitivity and reduce specificity, which can result in more episodes being opened but with increased false positives. A longer opening time, however, may reduce sensitivity and increase specificity, which can result in fewer episodes being opened but the risk of failing to detect VT or VF would increase. The selected time can determine the number of segments based on the duration of the segments and the amount of overlap between segments. For example, six segments would be needed to achieve an opening time of about fifteen seconds using 4.8 second segments with 50% overlap.

Similarly, the number of consecutive segments in a string for confirming VF or VT can be based on time. In some embodiments, the VT confirmation is selected to be forty-five seconds to allow for a VT rhythm to spontaneously terminate and/or transient noise to subside. In some embodiments, the VF confirmation is selected to be five seconds to initiate the patient alert sequence and a potential shock more quickly if the patient alert sequence completes without the patient responding. A shorter confirmation time may result in more patient alert sequences being initiated but with more sequences being aborted by the patient. A longer confirmation time, however, may result in fewer patient alert sequences being initiated but the risk of failing to confirm actual VT or VF would increase.

In various embodiments, the string length or time duration for opening episodes and/or confirming VF/VT and/or the number of tolerated false negative segments are selected to meet time to treatment, accuracy, sensitivity and/or specificity criteria.

Figure 7:
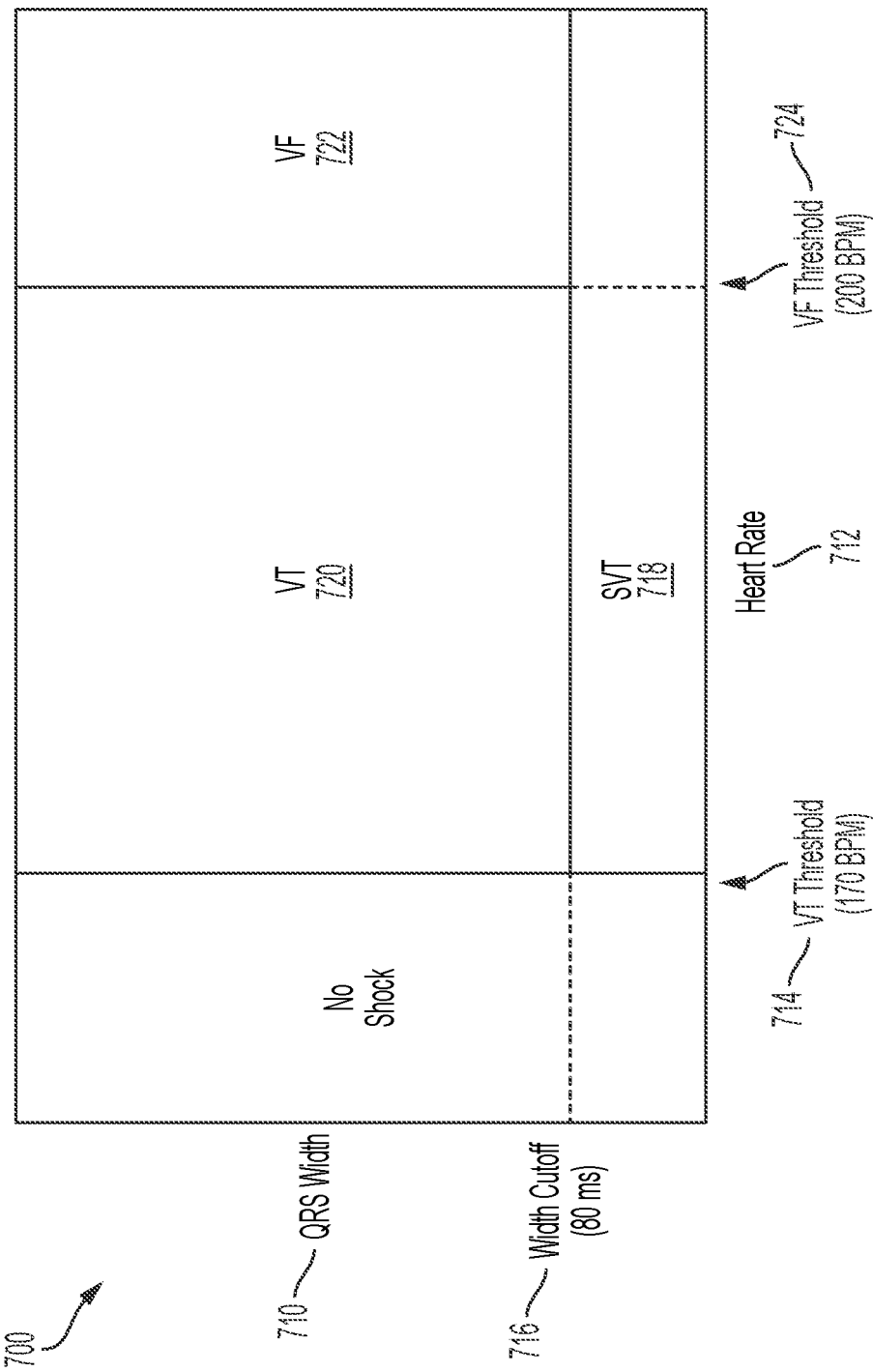
FIG. 7 is a diagram of a shock decision method used in a WCD in accordance with one or more embodiments.

Referring now to FIG. 7, a diagram of a shock decision method used in a WCD in accordance with one or more embodiments will be discussed. In one or more embodiments, WCD 100 can utilize a rhythm analysis algorithm (RAA) to make shock/no-shock decisions based on the patient's heart rate and QRS width according to graph 700. QRS 710 width is shown on the vertical axis, and heart rate 712 is shown on the horizontal axis. As shown in FIG. 7, all rhythms with a heartrate below the ventricular tachycardia (VT) threshold 714, for example 170 beats per minute (BPM), are considered non-shockable. All rhythms below the QRS width cutoff 716, for example 80 milliseconds (ms), are considered non-shockable as well. Above the VT threshold 714, narrow rhythms are classified as super ventricular tachycardia (SVT) 718. Fast, wide rhythms are classified either as ventricular tachycardia (VT) 720 or ventricular fibrillation (VF) 722, depending on the heart rate. For example, in some embodiments heart rate above a VF threshold 724 of 200 BPM with a QRS width above the QRS width cutoff threshold 716 would be classified as VF 722. Both VT 720 and VF 722 are considered shockable conditions. Table 1 below summarizes "zones" defining how WCD 100 can classify a patient's heart rhythm, according to some embodiments. In other embodiments, the heart rate and QRS width values for defining zones can be different. For example, in some embodiments the patient's physician may program the WCD 100 with the thresholds for each of these zones.

TABLE 1

No Shock, VT, SVT and VF Zones

| Parameter | No Shock | VT | VF | SVT |
|---|---|---|---|---|
| Heart Rate | <170 BPM | >170 BPM | >200 BPM | >170 BPM |
| QRS Width | — | >80 ms | >80 ms | <80 ms |

Referring now to FIG. 8, a diagram of an example QRS complex as part of a QRS width measuring process used in a WCD 100 in accordance with one or more embodiments will be discussed. FIG. 8 illustrates an example QRS complex 800. In one or more embodiments, an example method to measure the width of the QRS complex 800 can be as follows. First, the positive peak (R) 810 of the QRS complex 800 is found. The positive peak 810 is used as a reference point for measuring pulse width. Next, the two negative peaks, (Q) 812 and (S) 814 are found. Then, the value and location of the maximum slope between the two negative peaks is found. This is the first reference point for measuring pulse width. The point where the slope has dropped by a specific fraction is found. This is the second reference point used for measuring pulse width. The pulse width is then calculated as two times (2×) the interval between the first reference point and the second reference point. Example methods to measure QRS width are described in U.S. Pat. No. 9,592,403 which is incorporated herein by reference in its entirety.

Figure 9A:
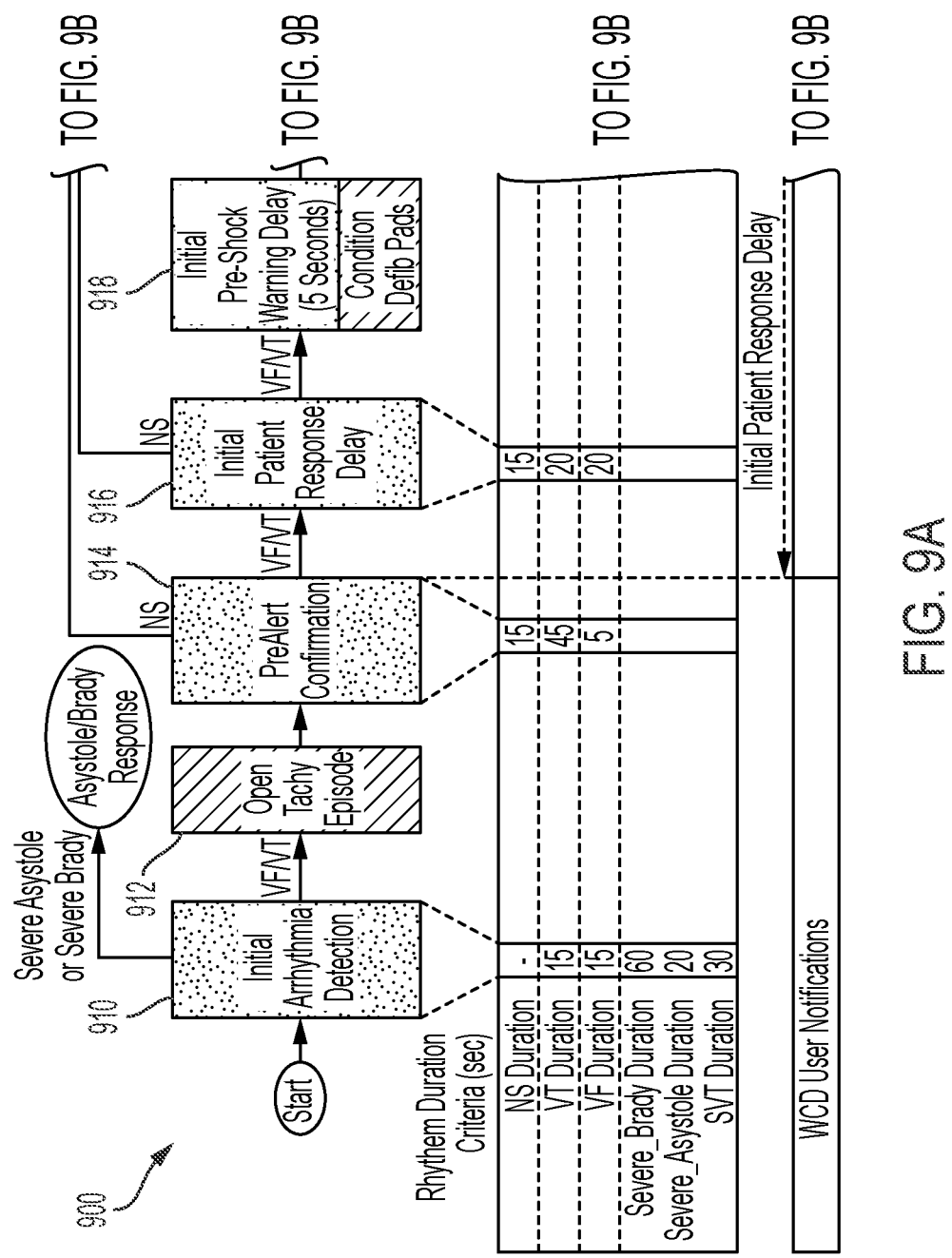
FIG. 9A through FIG. 9B illustrate a diagram of an extended confirmation time for ventricular tachycardia (VT) in accordance with one or more embodiments.
Figure 9B:
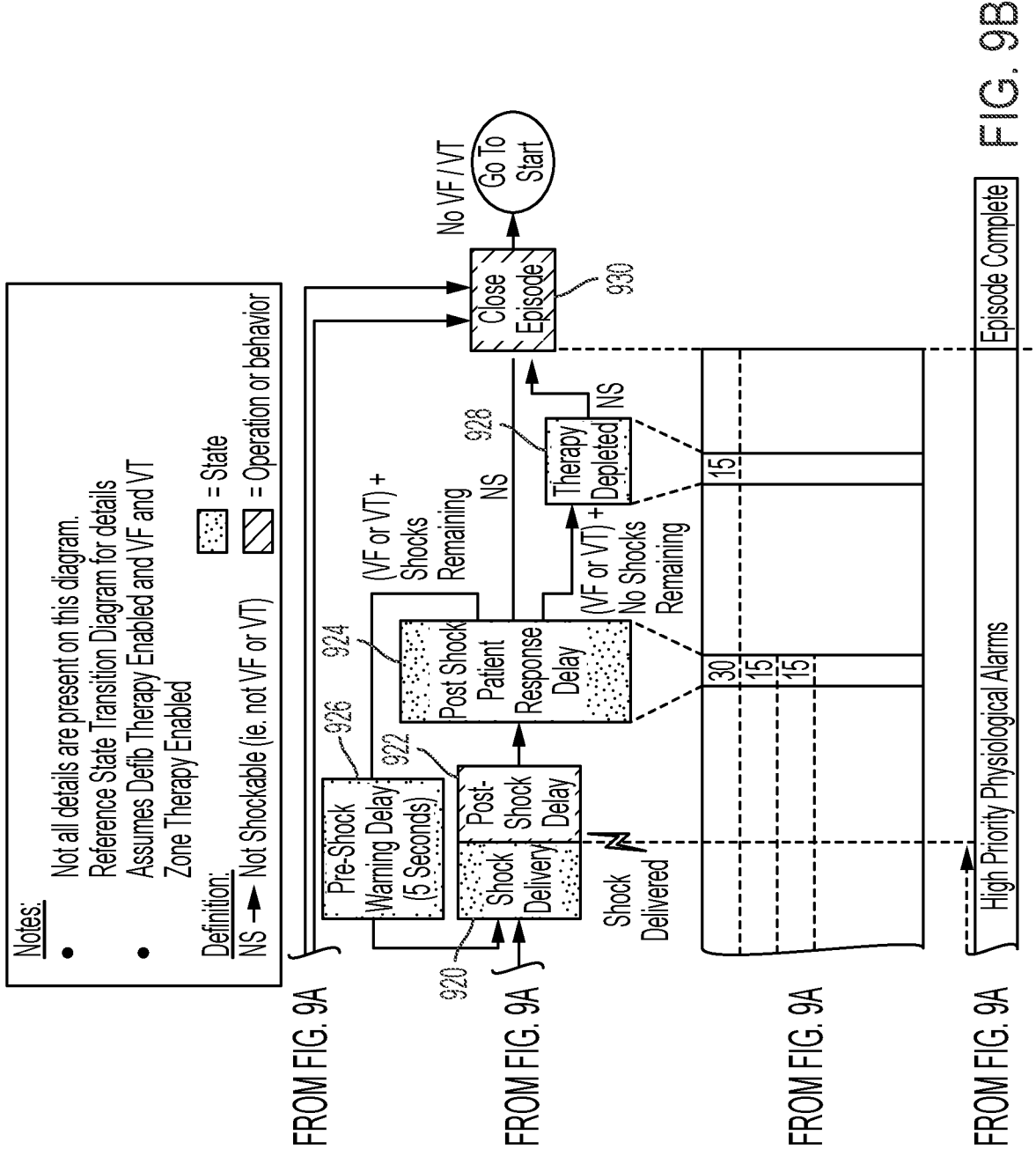

Referring now to FIG. 9A and FIG. 9B, a diagram illustrating an extended confirmation time for ventricular tachycardia (VT) in accordance with one or more embodiments will be discussed. In method 900, arrhythmia detection starts with a 15 second initial arrhythmia detection period at block 910. If the rhythm is detected as being shockable for 15 seconds, then an episode is opened at block 912 After an episode is opened, there is a pre-alert confirmation period at block 914 before an alarm is given. In some embodiments, for VF the confirmation period at block 914 is five seconds and for VT the confirmation period at block 914 is 45 seconds. In other embodiments, different confirmation periods may be utilized. The WCD 100 alarms for a period of time referred to as the Initial Patient Response Delay at block 916. If the patient 110 does not respond, then a shock is given at block 920 after an Initial Pre-Shock Warning Delay at block 918 which may be, for example, five seconds. A Post Shock Delay at block 922 occurs after shock delivery, followed by a Post Shock Patient Response Delay at block 924. Depending on the state of VF or VT and whether there are shocks remaining to be delivered by WCD 100, another shock delivery may occur at block 920 after Pre-Shock Warning Delay at block 926. For example, the energy to deliver one or more shocks can be stored in the battery 142 to charge the defibrillator capacitor 136, which can comprise one or multiple capacitors in some embodiments. The amount of energy stored in battery 142 can be sufficient to deliver one or more shocks during a given episode until the energy stored in the battery 142 is depleted. After a first shock, if there is enough energy in the battery 142, the defibrillator capacitor 136 can be recharged one or more times to deliver one or more additional shocks. In some embodiments, the defibrillator capacitor 136 is recharged after every shock, and it typically takes about six seconds to charge the defibrillator capacitor 136 for each shock. The only physical limit to the number of shocks that can be delivered is the energy in the battery 142. If the battery 142 has enough energy remaining to charge the defibrillator capacitor 136 one or more times, then WCD 100 can be considered as having remaining shocks to be delivered during an episode. Multiple shocks can be delivered during an episode until the WCD 100 determines that an additional shock would not be effective. In some embodiments, the WCD 100 stops delivering shocks after five shocks have been delivered. Application of multiple shocks can occur via a loop comprising block 920, block 922, block 924, and block 926. This loop can be repeated depending on the state of VF or VT and whether there are any remaining shocks to be delivered based on the amount of energy remaining in the battery 142. If therapy is depleted at block 928, meaning there is not enough energy left in the battery 142 to deliver another shock, or if there is no longer VF or VT, the episode can be closed at block 930. After an episode, the battery 142 and/or the defibrillator capacitor 136 can be recharged for future use.

If noise is present on the signal, WCD 100 can use the VT confirmation time for both VT and VF rhythm types. In some embodiments, methods of detecting noise in an ECG signal can be as disclosed in U.S. Pat. No. 9,757,581 which is incorporated herein by reference in its entirety. In some embodiments, a slow alarm pathway when ECG noise is detected can be as disclosed in U.S. Patent Application No. 62/538,159 filed Jul. 28, 2017 which is incorporated herein by reference in its entirety.

Figure 10:
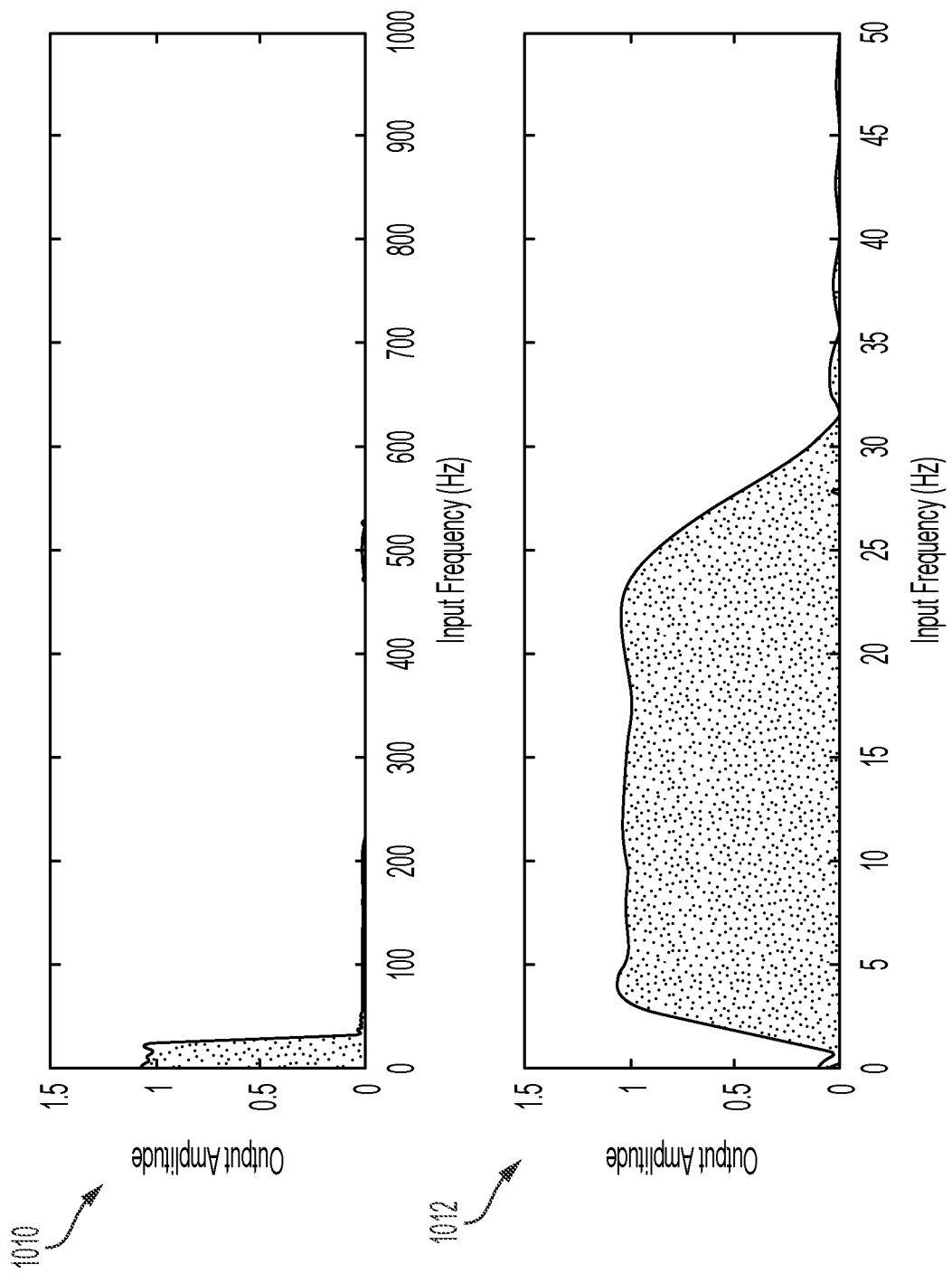
FIG. 10 is a diagram of filter responses applied to ECG data in a WCD in accordance with one or more embodiments.

Referring now to FIG. 10, a diagram of filter responses applied to ECG data in a WCD in accordance with one or more embodiments will be discussed. The QRS detector algorithm may be utilized with robust filtering including fixed finite impulse response (FIR) filters and an adaptive matched filter. In some embodiments, ECG data presented to the rhythm analysis algorithm implemented by WCD 100 is initially filtered with a fixed 2.75 Hz FIR high pass filter and a fixed 25 Hz FIR low pass filter. FIG. 10 illustrates the frequency response of these filters. The frequency response of the algorithm data is shown on graph 1010, and the frequency response of a zoom in passband filter is shown on graph 1012.

In some embodiments, the ECG data that is fed to the QRS detector in processor 138 is also filtered with a matched filter. Since the QRS waveform has a known shape, the matched filter can be used to identify the QRS waveform in the incoming ECG data. Embodiments of such a matched filter can be as described in U.S. patent application Ser. No. 15/724,317 filed Oct. 4, 2017 which is incorporated herein by reference in its entirety.

In some embodiments, a wearable cardioverter defibrillator, WCD 100, includes electrodes that render an ECG signal of the patient 110, and a processor 138 that receives ECG data are derived from the rendered ECG signal. The processor 138 may filter the received ECG data with a matched filter or a matched difference filter to detect QRS complexes and can compute a heart rate from the detected QRS complexes. The matched filter or matched difference filter itself can have coefficient values associated with a baseline QRS complex, which enhances detection.

Processor 138 renders the ECG signal internally and can include an optional initial filter. If provided, the initial filter may perform one or more types of filtering to the rendered ECG signal, such as passband filtering between 2.75 Hz to 25 Hz to remove artifacts at different frequencies, etc. The initial filter can be implemented by a conventional Finite Impulse Response (FIR) filter. In other embodiments, the initial filter can be provided within processor 138, operating digitally. In some embodiments, QRS complexes may be detected from outputs of the filters, and a heart rate (HR) can be computed from the detection results.

Figure 11:
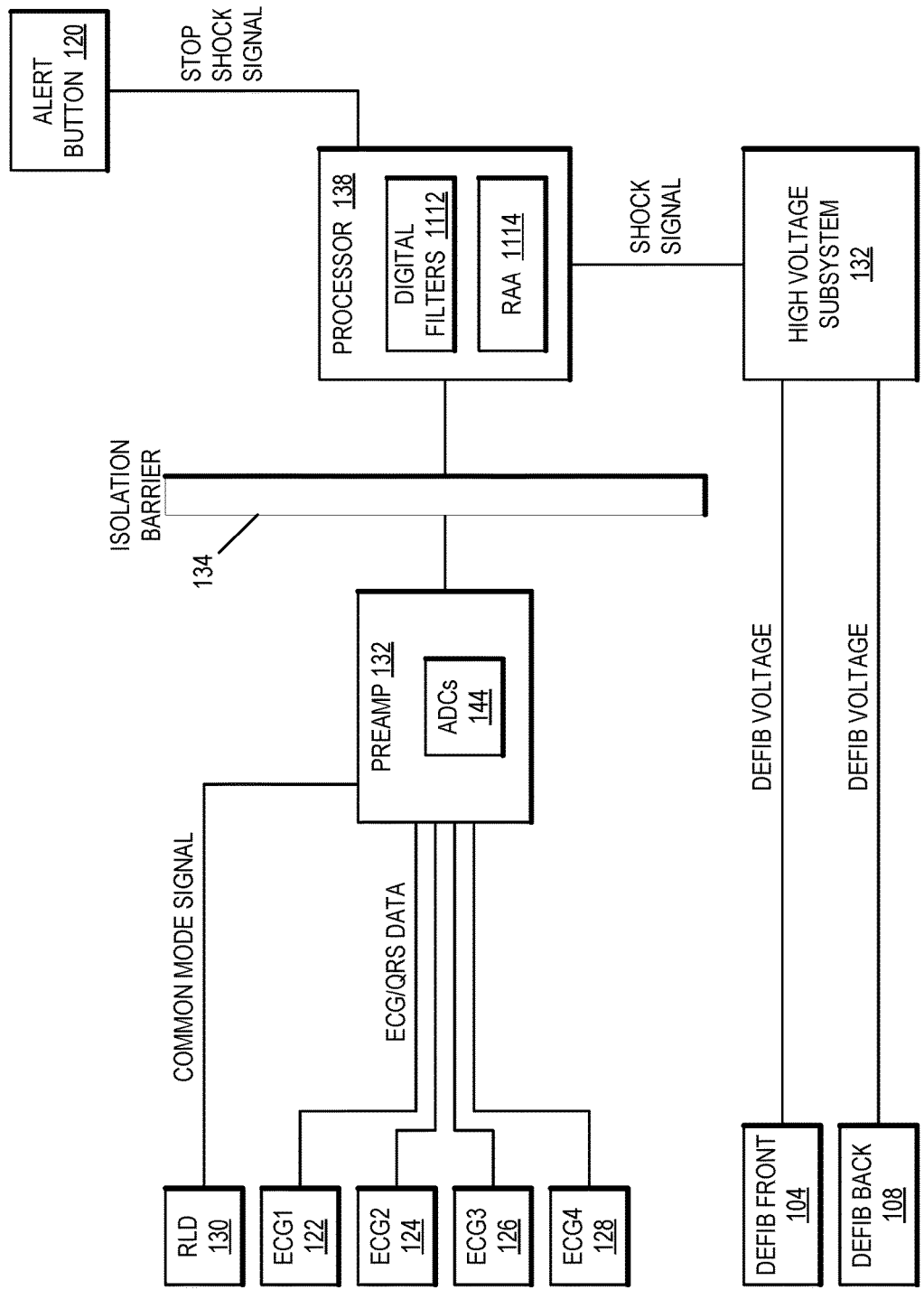
FIG. 11 is a diagram of a WCD that can operate with a lower false alarm rate in accordance with one or more embodiments.

Referring now to FIG. 11, a diagram of a WCD that can operate with a lower false alarm rate in accordance with one or more embodiments will be discussed. The WCD 100 shown in FIG. 11 incorporates one or more of the features discussed herein to enhance ECG and QRS complex signal data detection along with heart rate data detection in order to achieve a lower false alarm rate. The ECG electrodes, ECG1 122, ECG2 124, ECG3 126, and ECG4 128, can comprise silver or silver plated copper electrodes that "dry" attach to the skin of the patient 110. The ECG electrodes provide ECG/QRS data to preamplifier 132. The preamplifier 132 may have a wide dynamic range at its input, for example +/−1.1 V which is much larger than the amplitude of the ECG signals which are about 1 mV. The preamplifier includes analog-to-digital converters (ADCs) 144 to convert the ECG signals into a digital format. A right-leg drive (RLD) electrode 130 is used to provide a common mode signal so that the ECG signal from the ECG electrodes may be provided to preamplifier 132 as differential signals. The digital ECG signals are provided from the preamplifier 132 eventually to the main processor 138 of monitor 116 via an isolation barrier 134 which operates to electrically isolate the preamplifier 132 and the ECG signals from the rest of the circuitry of WCD 100.

The processor 138 processes the digital ECG/QRS data received from the preamplifier 132 with one or more digital filters 1112. Since the preamplifier 132 has a wide dynamic range that is much wider than the amplitude range of the ECG signals, digital filters 1112 may be utilized to process the ECG/QRS data without concern for clipping the incoming signals. One of the digital filters 1112 may include a matched filter to facilitate identification of QRS pulses in the incoming data stream. The wide dynamic range of the preamplifier 132 allows at least most of the ECG filtering to happen in software without the signal being clipped. Digital filters 1112 can be very effective at removing artifacts from the ECG/QRS data and may contribute to the enhanced false positive performance, that is a lower false positive rate, of the WCD 100 according to embodiments as described herein.

The processor 138 can apply the rhythm analysis algorithm (RAA) 1114 using QRS width information and heart rate data extracted from the digital ECG data using the segment-based processing analysis 600 of FIG. 6 and the QRS width versus heart rate graph 700 of FIG. 7 to make a shock or no-shock determination. The RAA 1114 receives the digitized ECG signal and calculates the heart rate and QRS width for each segment. The digitized ECG signal is passed over the isolation barrier 134, and the heart rate is derived from the digitized ECG signal. The heart rate and QRS width are used for making a shock/no-shock decision for each segment, which then can lead to an alarm and a shock. In the event a shockable event is identified, the processor 138 will open a tachycardia episode to start the shock process according to method 900 of FIG. 9A and FIG. 9B. Unless the patient 110 provides a patient response using the stop button 120 or user interface 140 to send a stop shock signal to the processor 138 to intervene before the shock is applied, the processor 138 can send a shock signal to the high voltage subsystem 132 which will apply a defibrillation voltage across the defib front electrode 104 and the defib back electrode 108 to apply one or more therapeutic shocks until there is no longer any shockable event (VT or VF) or until the energy in the battery 142 is depleted.

In one or more embodiments of the WCD 100, the digital filters 1112 coupled with the wide dynamic range of the preamplifier 132 of the ECG front end circuitry 400 may allow analysis of signals that otherwise would be clipped in systems with a more limited dynamic range. In addition, the matched filter of the digital filters 1112 preferentially highlights complexes similar to the patient's normal rhythm. As a result, artifacts that otherwise may be difficult to discriminate using other methods may be significantly attenuated by the matched filter to result in a lower false alarm rate of the WCD 100.

An example for computing outputs for a filter may be as follows, for example for a matched filter.

$$\text{Output}(n) = \sum_{m=0}^{length(f)} f(m) * g(m-n)$$

The above equation is similar to one for convolution, and in particular discrete convolution. The convolution of two finite sequences is defined by extending the sequences to finitely supported functions on the set of integers. In the above equation, f(m) are the data values of the ECG signal. While filter equation is similar to convolution, it is not identical to it. Indeed, while convolution uses the indexes g(n-m), a matched filter uses them in reverse order, which is also time order g(m-n). Moreover, for the matched filter in the filter equation, go are the coefficient values that define the kernel, and are chosen from a representation of the QRS signal that is to be detected. In other words, for a QRS detector the plot of the matched filter coefficients would look like a QRS complex. Rather than being frequency selective, a matched filter is sensitive to a specific shape.

Matched filtering according to embodiments enhances ECG detection, for example by detecting a higher number of the QRS complexes. Matched filters for detecting QRS complexes are suitable for WCD 100. Most ECG monitors use adhesive electrodes, and if the ECG signal is too noisy, then better skin preparation is likely the best remedy. On the contrary, with the WCD 100 described herein, extreme noise can be tolerated even with using "dry" electrodes, which potentially can be very noisy. Patient motion can cause problems when the "dry" electrodes move relative to the patient's skin which can cause a motion artifact in the ECG. Thus, using matched filtering techniques, operation of the WCD 100 would not stop notwithstanding any and all artifacts. Additionally, a matched filter can be suitable for segment-based ECG processing as shown in and described with respect to FIG. 6, above. When continuous processing is applied, an adaptive filter may be more appropriate.

It is noted that the features of WCD 100 described above may contribute to a lower false alarm rate, thereby reducing the number of times that WCD 100 provides an alarm to the patient 110 alerting of a shock about to be applied that is unnecessary. For example, in one or more embodiments any one or more of the features of WCD 100 may contribute to WCD 100 having an average false alarm rate of less than one false alarm event every ten patient-days. Any one or more of the features of WCD 100 also may contribute to WCD 100 being required to store data from patient episodes an average of less than one every ten patient-days, thereby reducing the amount of storage need for the data and requiring less analysis of the patient episode data by medical professionals. In addition, any one or more of the features of WCD 100 also may contribute to WCD 100 requiring fewer patient interactions, for example requiring the patient 110 to intervene and stop a false alarm event using alert button 120.

In addition to the above described features of WCD 100, in accordance with one or more embodiments, any one or more of the following features of WCD 100 described below also can contribute to a lower false alarm rate. In one or more embodiments, the rhythm analysis algorithm utilized by WCD 100 measures the heart rate and QRS width for all channels, for example four channels in some embodiments, excluding those with obvious noise. In some embodiments, the QRS width is simply taken from the channel that gives the widest measured width and applied to the rhythm analysis algorithm as described with respect to FIG. 7, above.

In some embodiments, the heart rate channel selection is a multi-step process. For example, embodiments of the overall channel selection process are described in U.S. Application No. 62/630,398 which is incorporated herein by reference in its entirety. As described for embodiments of the 62/630,398 application, an early operation is to estimate the heart rate error using the heart rate "Agreement" and QRS "Organization." The Agreement is an assessment of whether an individual channel is consistent with other channels. The QRS Organization is a measure of whether the morphology of the complexes is similar throughout the segment 618. Segments 618 with a high Agreement and Organization are judged to have less heart rate error. As described for embodiments of the 62/630,398 application, in another operation, if the heart rate error is estimated to be too high, then the R-R intervals between QRS complexes 800 are "pooled" and the mode, the most common, R-R interval is used for determining the heart rate. For example, it is possible that the chosen heart rate does not correspond with the heart rate calculated for any given channel, which may raise questions. The processor may detect sequential peaks within the ECG signal, measure durations of time intervals between the peaks, including between non-sequential peaks, and identify a representative duration. The representative duration is the one that occurs the most often, i.e., the mode. Then a heart rate can be computed from a duration indicated by the representative duration and, if the heart rate meets a shock condition, the WCD 100 may deliver a shock to the patient 110. The representative duration can be close to a good R-R interval measurement of a patient, notwithstanding any noise in the ECG signal. A WCD 100 incorporating this method may have logic for deciding when to use the heart rate mode or when to use a simpler method. The mode tends to be useful when there is a substantial disagreement in the heart rate between channels and there is not an obvious reason for disqualifying one or more channels such as a dislodged ECG lead. The pooling process is described in U.S. Application No. 62/501,009 filed May 3, 2017 and is child application Ser. No. 15/948,884 filed Apr. 9, 2018 which are incorporated herein by reference in their entireties.

Thus, in one or more embodiments WCD 100 is designed to select the ECG channel judged to have the least heart rate error regardless of noise. In such an approach, noise on the signal may or may not interfere with the heart rate measurement. It is noted that heart rate data may be less susceptible to noise than ECG data. As a result, using heart rate data as part of the RAA process to determine if a patient is experiencing a shockable cardiac event can mitigate and/or reduce the false alarm rate of the WCD 100.

In some embodiments, accelerometer-based motion analysis can preclude a shock decision while a patient is walking while wearing the WCD 100. The hub 114 may include accelerometer 414 to provide accelerometer information to an Accelerometer Algorithm (AA). In some embodiments, the accelerator algorithm may be implemented as disclosed in U.S. Patent Application No. 62/446,820 filed Jan. 16, 2017 which is incorporated herein by reference in its entirety. Embodiments of the AA will cause the Rhythm Analysis Algorithm (RAA) to not classify a segment 618 with a shock result if the AA judges that the patient 110 is walking.

Since walking is a common activity, walking is easy to detect using the AA. Detection of walking can provide a definitive indication that the patient 110 is not in cardiac arrest. Moreover, patient movement such as walking tends to create ECG artifacts that could confuse the RAA and cause a false shock alarm. When WCD 100 utilizes embodiments of the AA, the RAA will return a no-shock result while the patient 110 is walking thereby reducing or avoiding false alarms at a time when a typical WCD might otherwise be prone to false alarms.

In some embodiments, the AA can be configured to detect other types of patient motion in addition to walking. For example, a patient 110 in cardiac arrest will not be moving voluntarily but may exhibit reflexive skeletal muscle convulsions in which case the patient 110 may appear to gasp for breath in a manner known as agonal breathing. In addition, a patient 110 may experience cardiac arrest in a moving vehicle, and WCD 100 can be configured to not mistakenly inhibit therapy because of that motion.

In some embodiments, WCD 100 can be configured to detect other voluntary patient motion such as running, riding a bicycle, dancing, performing calisthenics, exercising on a stepper or elliptical machine, and so on, that would indicate that the patient 110 is not in cardiac arrest, while still rejecting movements that are consistent with a person in cardiac arrest such as reflexive skeletal muscle convulsion and agonal breathing described above. In such embodiments, WCD 100 can be configured to prevent false shock alarms for a wide range of patient activities in addition to walking.

In some embodiments, the WCD 100 is configured to have noise detection that is capable of distinguishing high-amplitude artifacts from QRS complexes 800. Example noise detection is disclosed in U.S. patent application Ser. No. 15/861,463 filed Jan. 3, 2018 which is incorporated herein by reference in its entirety. In embodiments as described in the Ser. No. 15/861,463 application, the WCD 100 can detect high amplitude noise such as QRS complexes or a baseline shift larger than a threshold such as 5 mV, and high frequency noise as a number of baseline crossings or number of extremely narrow ECG peaks greater than a threshold. When high-frequency noise is present on the signal and the patient 110 has an apparent shockable rhythm, in some embodiments the WCD 100 uses the VT pathway as described with respect to FIG. 9A and FIG. 9B above which has an extended confirmation time. When high-amplitude noise is present, in some embodiments the WCD 100 classifies the segment as "Noisy" rather than shock/no-shock.

In some embodiments, the WCD 100 is configured to utilize "Sticky" leads-off and noise processing detects periods of leads-off and noise and precludes rhythm analysis until the signals have cleared up. The WCD 100 can be configured to keep a circular buffer of noise analysis results, and if the number of the "Noisy" results exceed a threshold, then the WCD 100 enters a "Noise State". For example, in some embodiments, if two out of the last five analysis results are Noisy, then the WCD 100 enters the Noise State. Further rhythm analysis is inhibited while the WCD 100 is in the Noise State. The WCD 100 stays in the Noise State until five successive segments 618 yield a non-noisy result.

In some embodiments, if one ECG lead is detected as being "off", that is not touching the patient's skin, then the vectors derived from that electrode are excluded from further analysis. The WCD 100, however, continues to analyze the remaining vectors. Further, in some four-channel embodiments, if two ECG leads are detected as being "off" then the segment 618 is marked as Analysis Not Possible (ANP). If three out of five segments 618 are marked as ANP, then the WCD 100 enters the ANP state. Further rhythm analysis is suspended while the WCD 100 is in the ANP state. The WCD 100 stays in the ANP state until five successive segments 618 are detected not to be ANP.

Both the Noise State and the ANP state may be referred to as being "sticky" in some embodiments because once the WCD 100 enters either state, it is relatively difficult for WCD 100 to leave that state. This is so because ECG signals actually may be corrupted without tripping either the leads-off or the noise thresholds. If some segments 618 trip either a noise or leads-off threshold, it is likely that subsequent segments 618 may be corrupted even if the WCD 100 is unable to detect the corruption. To avoid this problem, in some embodiments the WCD 100 is configured to wait for a series of apparently clean segments before resuming analysis. Embodiments of this approach are described in more detail in U.S. Patent Application No. 62/538,145 filed on Jul. 28, 2017 which is incorporated herein by reference in its entirety.

In general, the wearable cardioverter defibrillator WCD 100 as disclosed herein is capable of operating with a reduced false alarm rate. Conventional WCDs analyze patient signals to determine if the patient is experiencing a cardiac arrest. If a VT/VF arrest is suspected, the WCD 100 will alarm to warn the patient and bystanders of an impending shock. Conventional WCDs often alarm inappropriately, that is when the patient is not in cardiac arrest. The Zoll LifeVest is the only WCD with published clinical performance. It has been discovered that the Zoll LifeVest WCD gives an inappropriate shock alarm about once every three patient-days on average. The Zoll Lifevest 4000 Operator's manual documents a WCD clinical study in which 13 patients wore WCDs for a collective total of 735 patient-days and experienced inappropriate shock alarms every 3.4 patient-days. These alarms can be distressing for the patient and, if the patient does not take action to intervene during a false alarm, an unnecessary shock could be applied. See for example, Olgin JE, Pletcher MJ, Vittinghoff E, et al., *"Wearable Cardioverter-Defibrillator after Myocardial Infarction,"* N Engl J Med 2018 Sep. 27; 379(13):1205-1215.

Because WCD patients are conscious, ambulatory people who go about their daily lives, sensor signals may experience artifacts from patient motion or from the environment. It is believed that such artifacts may cause the conventional WCD to incorrectly judge the patient 110 to be in cardiac arrest and lead to inappropriate alarms. Occasionally, conventional WCDs may misinterpret the patient's ECG signal, mistaking a non-shockable rhythm for a shockable rhythm. A recent publication by Schuhmann et al., *"Experience with the wearable cardioverter defibrillator (WCD) in high risk cardiac patients from a German single center cohort"*, Heart Rhythm 2016; 13(5):S254 showed that 97% of WCD false alarms were due to noise or artifacts and only 3% were true ventricular arrhythmias.

A recent clinical study of WCD Performance for Clinical Review, Sullivan et al., *"A Novel Wearable Cardioverter Defibrillator With Reduced False Alarm Rate,"* AHA 2017 abstract, included 50 patients who wore embodiments of WCD 100 according to the present disclosure for a total of 82 patient-days. No false shock alarms were given during this study. Statistically, it can be stated with 95% confidence that WCD 100 gives inappropriate shock alarms less than once every 27 patient-days.

In some embodiments, in order to assess the effect of device-triggered episodes, the WCD 100 stores an episode such as a short clip or duration of the ECG data when the WCD 100 detects a potentially shockable rhythm. If the rhythm spontaneously converts, or if the algorithm changes its shock decision, or if the patient 110 presses the divert/alert/stop shock button, then the patient 110 does not receive a shock. Even though the patient 110 is not shocked, the episode is stored for analysis. Stored episodes can be of diagnostic value to clinicians.

In contrast, with the Zoll LifeVest, device-triggered episodes are likely of limited clinical value because they are almost always due to noise, not a true cardiac arrhythmia. Because of the low false alarm rate embodiments of the WCD 100 of the present disclosure, fewer episodes due to noise will need to be stored. The episodes that are stored are more likely to represent a cardiac event that is of clinical interest. In the Sullivan study cited above, only one patient generated any episodes due to noise, and that patient is one who would probably be contraindicated for a WCD because of the type of pacemaker that patient had. Accordingly, the low false alarm rate of WCD 100 may apply to cardiac patients with a low ejection fraction, for example less than about 40%, who are wearing the WCD 100 during normal daily activities, although the scope of the disclosed subject matter is not limited in this respect.

As discussed herein, WCD 100 has a low false alarm rate. Furthermore, WCD 100 also has a low false episode rate. When WCD 100 makes a determination that a patient 110 has an arrhythmia, WCD 100 opens an episode and begins to store data related to the episode. For example, processor 138 of monitor 116 stores the episode data in a non-volatile or flash memory such as an internal memory or in a removable memory card such as Secure Digital (SD) card and/or Multimedia Card (MMC) (SD/MMC) or similar. If the arrythmia persists, then the WCD 100 generates an alarm. If the patient does not respond to the alarm within a predetermined period of time to intervene and stop the impending shock, then the WCD 100 delivers a therapeutic shock to the patient 110. Episode data is stored so that a physician can review the episode data to analyze what the patient's heart rhythm looked like during the episode in order to understand what is wrong with the patient even when a shock is not delivered.

False episodes may be incurred due to noise or signal artifacts just like false alarms. False episodes can be annoying to the physician because there could be nothing wrong with the patient's heart even though an episode occurred. As a result, the physician may need to review a large number of false episodes in order to find one true episode from a set of episodes. Sifting through such a large number of false episodes, however, may be a tedious and inefficient task for the physician, and as a result the physician may be disinclined to review the stored episodes at all if the vast majority of them are merely due to noise and not any issue with the patient's heart. Thus, providing a WCD 100 with a low false episode rate can facilitate physician review of the patient's episode data.

In accordance with one or more embodiments, the same mechanisms discussed herein that contribute to WCD 100 having a low false alarm rate also contribute to WCD 100 having a low false episode rate. Additionally, unnecessary shocks also can be problematic. A WCD that is confused by noise on the ECG would also be more prone to giving unnecessary shocks. Unnecessary shocks can be very traumatic for the patient 110 because the shocks can be painful, and it is possible that an unnecessary shock could trigger the patient 110 into a life-threatening arrhythmia. In accordance with one or more embodiments, the same mechanisms discussed herein that contribute to WCD 100 having a low false alarm rate also contribute to WCD 100 having a low unnecessary or false shock rate.

It should be noted that although this disclosure describes various embodiments, after careful review of this disclosure one skilled in the art will recognize that other embodiments also can yield a low false alarm rate. For example, some of the described embodiments employ a garment or support structure 112 that holds the ECG electrodes in proximity to the patient's skin. In other embodiments, techniques described in this disclosure could be implemented in devices that adhesively attach to the patient's skin or use a combination of adhesive pieces and removable pieces. In other embodiments, a low false alarm rate can be achieved by incorporating additional patient monitoring parameters. For example, ECG analysis can be coupled with a pulse detection circuit to confirm cardiac arrest before alarming the patient 110.

The following examples may be implemented in accordance with one or more embodiments. In example one, a wearable cardioverter defibrillator (WCD) comprises a plurality of electrocardiography (ECG) electrodes, a right-leg drive (RLD) electrode, and a plurality of defibrillator electrodes to contact the patient's skin when the WCD is delivering therapy to the patient, a user interface, a preamplifier coupled to the ECG electrodes and the RLD electrode to obtain ECG data from the patient as one or more ECG vectors, a processor to receive ECG data from the preamplifier and an abort signal from the user interface, an isolation barrier to isolate the preamplifier from the processor, and a high voltage subsystem to provide a defibrillation voltage to the patient through the plurality of defibrillator electrodes in response to a shock signal received from the processor. The processor is to determine when a shock criterion is met based on the ECG data from the preamplifier, and to provide the shock signal in the event the shock criterion is met and the abort signal is not received within a predetermined time period of the shock criterion being met. In example two, the processor is to determine QRS width data and heart rate data from the ECG data, and to determine when the shock criterion is met based on the QRS width data and the heart rate data. In example three, the preamplifier includes one or more analog-to-digital converters (ADCs) to convert the ECG data into digitized ECG data that is provided across the isolation barrier to the processor. In example four, the one or more vectors comprises four vectors. In example five, the processor is to monitor the one or more ECG vectors, and is configured to determine when the shock criterion is met when one or more of the ECG vectors is noisy or when one or more of the plurality of ECG electrodes is in a lead-off condition. In example six, the preamplifier is configured to receive the ECG data as differential signals using a voltage of the RLD electrode as a common mode signal or a common mode potential. In example seven, the preamplifier has a dynamic range at an input that is an order of magnitude or greater than a magnitude of the ECG data. In example eight, the ECG data received by the processor from the preamplifier is processed using one or more digital filters. In example nine, one or more QRS pulses are identified in the ECG data using a matched filter in the processor to determine the QRS width data and/or the heart rate data. In example ten, one or more of the plurality of ECG electrodes comprises a dry electrode to directly contact the patient's skin without using a gel or an adhesive. In example eleven, one or more of the ECG electrodes comprises a silver disk or a silver plated copper disk. In example twelve, one or more of the ECG electrodes comprises a resistive electrode. In example thirteen, the processor is to process the ECG data received from the preamplifier in segments of ECG data, wherein the shock criterion is met when a string of a predetermined number of segments indicate a shock decision should be made. In example fourteen, the preamplifier is configured to obtain one or more impedance values between the ECG electrodes, and to provide digitized impedance values to the processor across the isolation barrier. In example fifteen, the processor incurs less than one false alarm indicating the shock criterion has been met every ten patient-days.

In example sixteen, a method to determine whether a defibrillation shock should be applied with a wearable cardioverter defibrillator (WCD) comprises receiving electrocardiography (ECG) data from a patient using the WCD with a preamplifier coupled to one or more ECG electrodes and a right-leg drive (RLD) electrode coupled to the patient's skin to obtain ECG data from the patient as one or more ECG vectors, receiving ECG data from the preamplifier with a processor through an isolation barrier to electrically isolate the preamplifier from the processor, determining with the processor if a shock criterion is met based on a combination of heart rate data and a width of one or more QRS pulses identified in the ECG data, signaling the patient that the defibrillation shock is about to be applied, and applying the defibrillation shock to the patient unless a stop shock signal is caused by the patient within a predetermined period of time after signaling the patient. In example seventeen, the method further comprises converting the ECG data into digitized ECG data and providing the digitized ECG data across the isolation barrier to the processor. In example eighteen, the one or more vectors comprises four vectors. In example nineteen, said determining when the shock criterion is met occurs even when one or more of the ECG vectors is noisy or when one or more of the ECG electrodes is in a lead-off condition. In example twenty, the method further comprises processing the ECG data with the processor using one or more digital filters. In example twenty-one, the method further comprises identifying the one or more QRS pulses in the ECG data using a matched filter in the processor. In example twenty-two, the method further comprises processing the ECG data with the processor in segments of ECG data, wherein the shock criterion is met when a string of a predetermined number of segments indicate a shock decision should be made. In example twenty-three, the method further comprises obtaining one or more impedance values between the ECG electrodes with the preamplifier, and providing digitized impedance values to the processor across the isolation barrier. In example twenty-four, the method further comprises incurring less than one false alarm indicating the shock criterion has been met every ten patient-days.

In example twenty-five, wearable cardioverter defibrillator (WCD) system comprises a support structure comprising a plurality of electrocardiography (ECG) electrodes, a right-leg drive (RLD) electrode, and a plurality of defibrillator electrodes to contact the patient's skin when the WCD is delivering therapy to the patient, a hub comprising a preamplifier coupled to the ECG electrodes and the RLD electrode to obtain ECG data from the patient as one or more ECG vectors, and an isolation barrier to electrically isolate the preamplifier, an alert button coupled to the hub, and a monitor coupled to the hub and comprising a processor to receive the ECG data from the preamplifier through the isolation barrier, and a high voltage subsystem to provide a defibrillation voltage to the patient through the plurality of defibrillator electrodes in response to a shock signal received from the processor in the event a shock criterion is met and a stop shock signal is not received from the patient via the alert button prior to application of the defibrillation signal within a predetermined period of time after the shock criterion is met. The processor is to determine if the shock criterion is met based on a combination of the heart rate data identified in the ECG data and a width of one or more QRS pulses identified in the ECG data. In example twenty-six, the preamplifier has a dynamic range at an input that is an order of magnitude or greater than a magnitude of the ECG data, wherein the dynamic range allows the ECG data received by the processor to be processed using one or more digital filters without clipping. In example twenty-seven, the one or more QRS pulses are identified in the ECG data using a matched filter in the processor. In example twenty-eight 28, the processor is to process the ECG data received from the preamplifier in periodic segments, wherein the shock criterion is evaluated for each of the segments of ECG data, and a shock decision is made when the shock criterion is met for a predetermined number of successive segments. In example twenty-nine, the processor incurs less than one false alarm indicating the shock criterion has been met every ten patient-days.

In example thirty, a wearable cardioverter defibrillator (WCD) comprises a plurality of electrocardiography (ECG) electrodes and a plurality of therapy electrodes, the plurality of ECG electrodes and the plurality of therapy electrodes arranged to operatively contact a patient's skin when the WCD is operably attached to the patient, an amplifier coupled to the plurality of ECG electrodes to obtain multi-vector ECG data from the patient, an energy storage device configured to store an electrical charge, a high voltage subsystem coupled to the energy storage device and the plurality of therapy electrodes, and a processor coupled to the amplifier, the high voltage subsystem, and a user interface. The processor is configured to issue an alarm if a shock criterion is met, wherein the alarm is issued with a false alarm rate of less than one false alarm in ten patient days, and cause the high voltage subsystem to discharge the stored electrical charge from the energy storage device to the patient in response to the patient failing to respond to the alarm via the user interface within a predetermined time. In example thirty-one, the WCD further comprises a right-leg drive (RLD) electrode coupled to the amplifier to provide a common mode reference for the multi-vector ECG data. In example thirty-two, the WCD further comprises an isolation barrier to isolate the amplifier from the processor, wherein the amplifier is configured to transmit a digitized version of the multi-vector ECG data across the isolation barrier to the processor. In example thirty-three, at least one parameter of the multi-vector ECG data comprises heart rate, QRS width, QRS organization, or accelerometer data, or a combination thereof. In example thirty-four, the processor is configured to determine QRS width, heart rate, or QRS organization, or a combination thereof, from the multi-vector ECG data.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment, removing one or more features from an embodiment, or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the operations, acts, or modalities of a method.

Although the claimed subject matter has been described with a certain degree of particularity, it should be recognized that elements thereof may be altered by persons skilled in the art without departing from the spirit and/or scope of claimed subject matter. It is believed that the subject matter pertaining to a wearable cardioverter defibrillator (WCD) with a low false alarm rate and many of its attendant utilities will be understood by the foregoing description, and it will be apparent that various changes may be made in the form, construction and/or arrangement of the components thereof without departing from the scope and/or spirit of the claimed subject matter or without sacrificing all of its material advantages, the form herein before described being merely an explanatory embodiment thereof, and/or further without providing substantial change thereto. It is the intention of the claims to encompass and/or include such changes.

What is claimed is:

1. A wearable cardioverter defibrillator (WCD), comprising:
   a plurality of electrocardiogram (ECG) electrodes adapted to contact a patient's skin while the patient is wearing the WCD;
   a high voltage subsystem to provide a defibrillation voltage to the patient through a plurality of defibrillator electrodes in response to a shock signal; and
   one or more processors to receive ECG data via the plurality of ECG electrodes, wherein the one or more processors are configured to:
      analyze multiple segments of the ECG data, wherein a segment of the ECG data comprises a portion of the ECG data,
      determine whether individual segments in a string of consecutive segments of the ECG data independently meet a shock criterion,
      in the event a predetermined number of segments in the string of consecutive segments of the ECG data meet the shock criterion, open an episode,
      determine whether an additional number of segments of the ECG data beyond the predetermined number of segments meets one or more confirmation criteria,
      in the event the additional number of segments of the ECG data meets the one or more confirmation criteria, confirm a shockable rhythm in the episode and initiate a patient alert sequence responsive to confirmation of a shockable rhythm, and
      provide the shock signal to the high voltage subsystem responsive to completion of the patient alert sequence and otherwise not providing the shock signal responsive to a patient responding to the patient alert sequence.

2. The WCD of claim 1, wherein the shock criterion comprises all segments in the string of consecutive segments being determined to indicate a shockable rhythm.

3. The WCD of claim 1, wherein the shock comprises a minimum number of the predetermined number of segments in the string of consecutive segments being determined to indicate a shockable rhythm.

4. The WCD of claim 3, wherein the string of consecutive segments is six segments, and the predetermined number of segments is five segments.

5. The WCD of claim 1, wherein the one or more confirmation criteria comprises all segments in the additional number of segments being determined to indicate a shockable rhythm.

6. The WCD of claim 5, wherein the shockable rhythm is VF and the additional number of segments in the additional number of segments is two segments for the confirmation criteria.

7. The WCD of claim 1, wherein the one or more confirmation criteria comprises a minimum number of segments in the additional number of segments being determined to indicate a shockable rhythm.

8. The WCD of claim 7, wherein the shockable rhythm is VT and the additional number of segments in the string of consecutive segments is nineteen segments for the confirmation criteria, and the minimum number of segments in the string of consecutive segments is fifteen segments.

9. The WCD of claim 1, wherein the one or more processors are configured to determine whether a segment of the ECG data indicates a shockable rhythm based at least in part on a heart rate and a QRS width determined from the segment.

10. The WCD of claim 1, wherein the one or more processors are configured to classify a segment of the ECG data into one of a plurality of types based at least in part on a heart rate and a QRS width determined from the segment.

11. The WCD of claim 10, wherein the plurality of types comprises VF, VT, and SVT.

12. The WCD of claim 11, wherein a segment determined to have a heart rate above 120 beats per minute (BPM) and a QRS width less than 80 milliseconds (ms) is classified as SVT.

13. The WCD of claim 1, wherein the segments of the ECG data comprise 4.8 seconds in duration.

14. A wearable medical system (WMS), comprising:
a support structure to be worn by a patient;
a plurality of electrocardiogram (ECG) electrodes coupled to the support structure and structured to contact a patient's skin while the patient is wearing the support structure; and
one or more processors to receive ECG data via the plurality of ECG electrodes, wherein the one or more processors are configured to:
   analyze multiple segments of the ECG data, wherein a segment of the ECG data comprises a portion of the ECG data,
   determine whether individual segments in a string of consecutive segments of the ECG data independently meet an arrhythmia criterion,
   in the event a predetermined number of segments in the string of consecutive segments of the ECG data meet the arrhythmia criterion, open an episode,
   determine whether an arrhythmia is confirmed in the episode when an additional number of segments of the ECG data beyond the predetermined number of segments meets one or more confirmation criteria,
   in the event the additional number of segments of the ECG data meets the one or more confirmation criteria, confirm the arrythmia in the episode and initiate a patient alert sequence responsive to a determination that the arrhythmia is confirmed, and
   otherwise not initiate the patient alert sequence responsive to a determination that the arrythmia is not confirmed.

15. The WMS of claim 14, wherein the one or more confirmation criteria comprises a minimum number of the predetermined number of segments in the string of consecutive segments being determined to indicate the arrhythmia.

16. The WMS of claim 15, wherein the string of consecutive segments is six segments, and the predetermined number of segments is five segments.

17. The WMS of claim 14, wherein the one or more confirmation criteria comprises a minimum number of segments in the additional number of segments being determined to indicate the arrhythmia.

18. The WMS of claim 14, wherein the one or more processors are configured to determine whether a segment of the ECG data indicates an arrhythmia based at least in part on a heart rate and a QRS width determined from the segment.

19. The WMS of claim 14, wherein the one or more processors are configured to classify a segment of the ECG data into one of a plurality of arrhythmias based at least in part on a heart rate and a QRS width determined from the segment.

20. The WMS of claim 19, wherein the plurality of arrhythmias comprises ventricular fibrillation (VF), ventricular tachycardia (VT), and supraventricular tachycardia (SVT).

21. The WMS of claim 20, wherein a segment determined to have a heart rate above 120 beats per minute (BPM) and a QRS width less than 80 milliseconds (ms) is classified as SVT.

* * * * *